United States Patent
Brugger et al.

(10) Patent No.: US 10,345,175 B2
(45) Date of Patent: Jul. 9, 2019

(54) PRESSURE MEASUREMENT DEVICES, METHODS, AND SYSTEMS

(71) Applicant: NxStage Medical, Inc., Lawrence, MA (US)

(72) Inventors: James M. Brugger, Newburyport, MA (US); Dennis M. Treu, Castle Rock, CO (US); Jeffrey H. Burbank, Boxford, MA (US); Scott W. Newell, Ipswich, MA (US); William J. Schnell, Libertyville, IL (US); Kenneth E. Buckler, Methuen, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 15/800,901

(22) Filed: Nov. 1, 2017

(65) Prior Publication Data

US 2018/0128698 A1    May 10, 2018

Related U.S. Application Data

(60) Continuation of application No. 15/219,334, filed on Jul. 26, 2016, now Pat. No. 9,835,509, which is a
(Continued)

(51) Int. Cl.
*G01L 9/00* (2006.01)
*G01L 19/00* (2006.01)
*A61M 1/36* (2006.01)

(52) U.S. Cl.
CPC .......... *G01L 9/006* (2013.01); *A61M 1/3639* (2013.01); *A61M 1/3641* (2014.02);
(Continued)

(58) Field of Classification Search
CPC ... B29C 45/261; B29C 45/2614; B29C 45/36; B29C 2045/363; B29C 33/485
See application file for complete search history.

(56) References Cited

U.S. PATENT DOCUMENTS 50,957 A * 11/1865 Richardson ........... B29C 33/485
425/468
3,046,788 A    7/1962 Laimins
(Continued)

FOREIGN PATENT DOCUMENTS

CN    2522849    11/2002
CN    102657520 A    9/2012
(Continued)

OTHER PUBLICATIONS

Decision by Patent Trial and Appeal Board on Case IPR2016-00744, Paper 11, U.S. Pat. No. 8,092,414B2, entered Jul. 28, 2016, pp. 1-19.
(Continued)

*Primary Examiner* — Joseph S Del Sole
*Assistant Examiner* — Emmanuel S Luk
(74) *Attorney, Agent, or Firm* — Potomac Law Group, PLLC; Mark Catan

(57) ABSTRACT

A pressure measurement pod for blood circuits can include a flexible, moveable, fluid-impermeable diaphragm and can be formed via either a one-shot or a two-shot molding process. A method of manufacturing a pressure measuring device can include providing first and second major mold parts having recesses defining major parts of a housing, and inserting pins in the first and second major mold parts, the pins being shaped to define a flow channel of a molded pressure measuring pod. One of the pins may have a major face that defines an internal surface of a diaphragm. The method may further include closing the first and second major mold parts with the pins therebetween and injection
(Continued)

molding a pressure pod housing. Finally, the pressure pod is removed from the mold parts and the pins are withdrawn from the flow channel.

20 Claims, 18 Drawing Sheets

Related U.S. Application Data division of application No. 14/115,924, filed as application No. PCT/US2012/040298 on May 31, 2012, now Pat. No. 9,551,625.

(60) Provisional application No. 61/544,266, filed on Oct. 6, 2011, provisional application No. 61/491,869, filed on May 31, 2011.

(52) U.S. Cl.
CPC ........ *A61M 1/3653* (2013.01); *A61M 1/3659* (2014.02); *G01L 9/0041* (2013.01); *G01L 19/003* (2013.01); *G01L 19/0023* (2013.01); *G01L 19/0046* (2013.01); *A61M 2205/3331* (2013.01); *A61M 2205/75* (2013.01); *A61M 2207/00* (2013.01)

(56) References Cited

U.S. PATENT DOCUMENTS

| | | | |
|---|---|---|---|
| 3,165,788 A * | 1/1965 | Davidson | B29C 45/36 249/125 |
| 3,418,853 A | 12/1968 | Curtis | |
| 3,713,341 A | 1/1973 | Madsen et al. | |
| 3,863,504 A | 2/1975 | Borsanyi | |
| 4,077,882 A | 3/1978 | Gangemi | |
| 4,140,337 A | 2/1979 | Arcella et al. | |
| 4,189,936 A | 2/1980 | Ellis | |
| 4,207,551 A | 6/1980 | Kautzky | |
| 4,209,391 A | 6/1980 | Lipps et al. | |
| 4,226,124 A | 10/1980 | Kersten | |
| 4,298,938 A | 11/1981 | Wang et al. | |
| 4,303,376 A | 12/1981 | Siekmann | |
| 4,353,368 A | 10/1982 | Slovak et al. | |
| 4,398,542 A | 8/1983 | Cunningham et al. | |
| 4,412,916 A | 11/1983 | Kell | |
| 4,444,198 A | 4/1984 | Petre | |
| 4,447,191 A | 5/1984 | Bilstad et al. | |
| 4,457,749 A | 7/1984 | Bellotti et al. | |
| 4,479,760 A | 10/1984 | Bilstad et al. | |
| 4,501,531 A | 2/1985 | Bilstad et al. | |
| 4,535,635 A | 8/1985 | Claren et al. | |
| 4,555,949 A | 12/1985 | Danby et al. | |
| 4,573,997 A | 3/1986 | Wisman et al. | |
| 4,576,181 A | 3/1986 | Wallace et al. | |
| 4,610,256 A | 9/1986 | Wallace | |
| 4,617,115 A | 10/1986 | Vantard | |
| 4,666,598 A | 5/1987 | Heath et al. | |
| 4,747,950 A | 5/1988 | Guinn | |
| 4,769,001 A | 9/1988 | Prince | |
| 4,770,787 A | 9/1988 | Heath et al. | |
| 4,795,440 A | 1/1989 | Young et al. | |
| 4,798,090 A | 1/1989 | Heath et al. | |
| 4,997,570 A | 3/1991 | Polaschegg | |
| 5,024,099 A | 6/1991 | Lee | |
| 5,044,401 A | 9/1991 | Giesler et al. | |
| 5,069,792 A | 12/1991 | Prince et al. | |
| 5,186,431 A | 2/1993 | Tamari | |
| 5,197,192 A | 3/1993 | Wylie et al. | |
| 5,354,530 A * | 10/1994 | Atkinson | B29C 33/0033 138/43 |
| 5,360,395 A | 11/1994 | Utterberg | |
| 5,391,248 A * | 2/1995 | Brain | A61M 16/04 128/207.14 |
| 5,417,673 A | 5/1995 | Gordon | |
| 5,440,932 A | 8/1995 | Wareham | |
| 5,456,675 A | 10/1995 | Wolbring et al. | |
| 5,536,237 A | 7/1996 | Prince et al. | |
| 5,554,113 A | 9/1996 | Novak et al. | |
| 5,571,970 A | 11/1996 | Mutoh et al. | |
| 5,602,339 A | 2/1997 | Wareham | |
| 5,614,677 A | 3/1997 | Wamsiedler et al. | |
| 5,643,205 A | 7/1997 | Utterberg | |
| 5,693,008 A | 12/1997 | Brugger et al. | |
| 5,700,415 A * | 12/1997 | Hiroki | B29C 33/485 249/152 |
| 5,722,399 A | 3/1998 | Chevallet et al. | |
| 5,738,334 A | 4/1998 | Proni | |
| 5,744,027 A | 4/1998 | Connell et al. | |
| 5,814,004 A | 9/1998 | Tamari | |
| 5,846,257 A | 12/1998 | Hood | |
| 5,924,584 A | 7/1999 | Hellstrom et al. | |
| 5,980,741 A | 11/1999 | Schnell et al. | |
| 6,014,800 A | 1/2000 | Lee | |
| 6,039,078 A | 3/2000 | Tamari | |
| 6,280,406 B1 | 8/2001 | Dolecek et al. | |
| 6,409,696 B1 | 6/2002 | Toavs et al. | |
| 6,440,080 B1 | 8/2002 | Booth et al. | |
| 6,463,813 B1 | 10/2002 | Gysling | |
| 6,517,508 B1 | 2/2003 | Utterberg et al. | |
| 6,523,414 B1 | 2/2003 | Malmstrom et al. | |
| 6,526,357 B1 | 2/2003 | Soussan et al. | |
| 6,579,253 B1 | 6/2003 | Burbank et al. | |
| 6,579,496 B1 | 6/2003 | Fausset et al. | |
| 6,589,482 B1 | 7/2003 | Burbank et al. | |
| 6,638,478 B1 | 10/2003 | Treu et al. | |
| 6,649,046 B2 | 11/2003 | Chevallet | |
| 6,764,460 B2 | 7/2004 | Dolecek et al. | |
| 6,857,326 B2 | 2/2005 | Specht et al. | |
| 6,957,588 B1 | 10/2005 | Kicher et al. | |
| 7,056,316 B1 | 6/2006 | Burbank et al. | |
| 7,121,143 B2 | 10/2006 | Malmstrom et al. | |
| 7,160,497 B2 * | 1/2007 | Krantz | B29C 33/485 264/328.11 |
| 7,331,346 B2 * | 2/2008 | Zocca | A61M 16/0051 128/207.14 |
| 7,337,674 B2 | 3/2008 | Burbank et al. | |
| 7,603,907 B2 | 10/2009 | Reiter et al. | |
| 7,708,051 B2 * | 5/2010 | Katsumi | G01L 9/0051 164/113 |
| 7,803,628 B2 | 9/2010 | Glocker | |
| 7,853,362 B2 | 12/2010 | Gray et al. | |
| 7,921,723 B2 | 4/2011 | Reiter et al. | |
| 8,060,190 B2 | 11/2011 | Sömmo et al. | |
| 8,086,323 B2 | 12/2011 | Reghabi et al. | |
| 8,092,414 B2 | 1/2012 | Schnell et al. | |
| 8,142,384 B2 | 3/2012 | Becker et al. | |
| 8,239,010 B2 | 8/2012 | Banet et al. | |
| 8,266,967 B2 | 9/2012 | Kitani et al. | |
| 8,287,480 B2 | 10/2012 | Sasaki et al. | |
| 8,375,797 B2 | 2/2013 | Beden et al. | |
| 8,471,659 B1 | 6/2013 | Flegel | |
| 8,491,518 B2 | 7/2013 | Schnell et al. | |
| 8,574,183 B2 | 11/2013 | Kopperschmidt | |
| 8,591,448 B2 | 11/2013 | Powers et al. | |
| 8,647,290 B2 | 2/2014 | Masala et al. | |
| 8,752,436 B2 | 6/2014 | Beck et al. | |
| 8,950,241 B2 | 2/2015 | Hedmann et al. | |
| 8,992,461 B2 | 3/2015 | Hedmann et al. | |
| 9,004,886 B2 | 4/2015 | Beck et al. | |
| 9,050,417 B2 | 6/2015 | Fini et al. | |
| 9,295,770 B2 | 3/2016 | Gagel | |
| 9,400,199 B2 | 7/2016 | Wolff | |
| 9,435,706 B2 | 9/2016 | Fini et al. | |
| 9,474,846 B2 | 10/2016 | Steger | |
| 9,610,393 B2 | 4/2017 | Rada et al. | |
| 9,694,126 B2 | 7/2017 | Hedmann et al. | |
| 9,757,505 B2 | 9/2017 | Lindley et al. | |
| 9,821,104 B2 | 11/2017 | Bocklet | |
| 9,855,380 B2 | 1/2018 | Ritter et al. | |
| 9,855,381 B2 | 1/2018 | Tényi et al. | |
| 9,931,456 B2 | 4/2018 | Rovatti et al. | |
| 10,016,555 B2 | 7/2018 | Finch et al. | |

(56) References Cited

U.S. PATENT DOCUMENTS

| | | | |
|---|---|---|---|
| 10,022,673 B2 | 7/2018 | Fulkerson et al. | |
| 10,024,747 B2 | 7/2018 | Russell et al. | |
| 10,058,694 B2 | 8/2018 | Norris et al. | |
| 2002/0007137 A1 | 1/2002 | Utterberg et al. | |
| 2002/0049412 A1 | 4/2002 | Madrid et al. | |
| 2002/0177786 A1 | 11/2002 | Balbo | |
| 2003/0115965 A1 | 6/2003 | Mittelstein et al. | |
| 2003/0126910 A1 | 7/2003 | Burbank | |
| 2004/0060359 A1 | 4/2004 | Wilson | |
| 2004/0068239 A1 | 4/2004 | Utterberg et al. | |
| 2005/0119597 A1 | 6/2005 | O'Mahony et al. | |
| 2005/0147525 A1 | 7/2005 | Bousquet | |
| 2005/0159710 A1 | 7/2005 | Utterberg | |
| 2005/0209563 A1 | 9/2005 | Hopping et al. | |
| 2005/0224405 A1 | 10/2005 | Neri et al. | |
| 2006/0122552 A1 | 6/2006 | O'Mahony | |
| 2007/0000333 A1 | 1/2007 | Brugger et al. | |
| 2007/0179422 A1 | 8/2007 | Schnell et al. | |
| 2007/0232980 A1 | 10/2007 | Felt et al. | |
| 2008/0175719 A1 | 7/2008 | Tracey et al. | |
| 2008/0228087 A1* | 9/2008 | Brugger | A61M 1/3626 600/485 |
| 2009/0007683 A1 | 1/2009 | Kaneko et al. | |
| 2009/0293588 A1 | 12/2009 | Riley et al. | |
| 2010/0084326 A1 | 4/2010 | Takesawa | |
| 2010/0222735 A1 | 9/2010 | Plahey et al. | |
| 2010/0331754 A1 | 12/2010 | Fulkerson et al. | |
| 2011/0066043 A1 | 3/2011 | Banet et al. | |
| 2011/0139704 A1 | 6/2011 | Choi et al. | |
| 2011/0152739 A1 | 6/2011 | Roncadi et al. | |
| 2012/0095351 A1 | 4/2012 | Klose et al. | |
| 2012/0130338 A1 | 5/2012 | Schnell et al. | |
| 2012/0306118 A1* | 12/2012 | Hayashi | B29C 45/44 264/249 |
| 2012/0312726 A1 | 12/2012 | Gagel | |
| 2012/0316799 A1 | 12/2012 | Gagel | |
| 2013/0006128 A1 | 1/2013 | Olde et al. | |
| 2013/0150768 A1 | 6/2013 | Sakamoto et al. | |
| 2013/0180339 A1 | 7/2013 | Brugger | |
| 2013/0261529 A1 | 10/2013 | O'Mahony | |
| 2013/0291970 A1 | 11/2013 | Schnell et al. | |
| 2014/0069857 A1 | 3/2014 | Brueckner | |
| 2014/0076058 A1 | 3/2014 | Brugger et al. | |
| 2014/0165733 A1 | 6/2014 | Jansson et al. | |
| 2014/0166579 A1 | 6/2014 | Gagel et al. | |
| 2014/0180261 A1* | 6/2014 | Nyman | A61M 25/0015 604/544 |
| 2014/0196798 A1* | 7/2014 | Tai | F16K 99/0057 137/15.19 |
| 2014/0246814 A1* | 9/2014 | Planta Torralba | B29C 49/20 264/537 |
| 2014/0299544 A1 | 10/2014 | Wilt et al. | |
| 2014/0319035 A1 | 10/2014 | Burbank et al. | |
| 2015/0129055 A1 | 5/2015 | Byler | |
| 2015/0343128 A1 | 12/2015 | Hogard et al. | |
| 2016/0045657 A1 | 2/2016 | Krause et al. | |
| 2017/0014077 A1 | 1/2017 | Maurer et al. | |
| 2017/0014565 A1 | 1/2017 | Wiktor et al. | |
| 2017/0021088 A1 | 1/2017 | Fulkerson et al. | |
| 2017/0095602 A1 | 4/2017 | Ishizaki et al. | |
| 2017/0106131 A1 | 4/2017 | Hörnig | |
| 2017/0182233 A1 | 6/2017 | Kloeffel et al. | |
| 2017/0196517 A1 | 7/2017 | Zhang | |
| 2017/0258975 A1 | 9/2017 | Fulkerson et al. | |
| 2017/0312417 A1 | 11/2017 | Noack et al. | |
| 2018/0001009 A1 | 1/2018 | Crawford et al. | |
| 2018/0080578 A1* | 3/2018 | Tai | F16K 99/0057 |
| 2018/0080843 A1 | 3/2018 | Funamura et al. | |
| 2018/0093033 A1 | 4/2018 | Crnkovich et al. | |
| 2018/0117234 A1 | 5/2018 | Neftel | |
| 2018/0133384 A1 | 5/2018 | Tokunaga et al. | |
| 2018/0184985 A1 | 7/2018 | Håkansson et al. | |
| 2018/0228959 A1 | 8/2018 | Thys | |
| 2018/0228961 A1 | 8/2018 | Takeuchi et al. | |
| 2018/0296745 A1 | 10/2018 | Olde et al. | |
| 2018/0318490 A1 | 11/2018 | Naruse et al. | |
| 2019/0001533 A1* | 1/2019 | Murphy | B29C 33/005 |

FOREIGN PATENT DOCUMENTS

| | | |
|---|---|---|
| CN | 202636924 U | 1/2013 |
| CN | 202699703 U | 1/2013 |
| CN | 102735392 B | 12/2014 |
| CN | 105214155 B | 8/2018 |
| DE | 102011103261 A1 | 11/2012 |
| EP | 0330891 B1 | 11/1992 |
| EP | 1723905 A2 | 11/2006 |
| EP | 2238996 A1 | 10/2010 |
| EP | 2550987 B1 | 1/2013 |
| EP | 2687247 A1 | 1/2014 |
| EP | 2526981 B1 | 2/2014 |
| EP | 2468324 B1 | 4/2014 |
| EP | 2397168 B1 | 5/2014 |
| EP | 2737917 A1 | 6/2014 |
| EP | 2737917 B1 | 6/2014 |
| EP | 2687247 B1 | 9/2014 |
| EP | 2792377 A1 | 10/2014 |
| EP | 2730302 B1 | 12/2014 |
| EP | 2609944 B1 | 1/2015 |
| EP | 2881130 A1 | 6/2015 |
| EP | 2881130 B1 | 6/2015 |
| EP | 2717938 B1 | 8/2015 |
| EP | 2931333 A1 | 10/2015 |
| EP | 3077087 A1 | 10/2016 |
| EP | 3266477 A1 | 9/2018 |
| FR | 2346238 A1 | 10/1977 |
| JP | 1982169336 A | 4/1982 |
| JP | 1984181162 | 10/1984 |
| JP | 61143069 | 6/1986 |
| JP | S625172 | 2/1987 |
| JP | S6429267 | 1/1989 |
| JP | 09024026 A | 1/1997 |
| JP | H0924026 | 1/1997 |
| JP | 2001353215 | 12/2001 |
| JP | 200595230 A | 4/2005 |
| JP | 2011167424 A | 9/2011 |
| JP | 2012000319 A | 1/2012 |
| JP | 2012152287 A | 8/2012 |
| JP | 2012152289 A | 8/2012 |
| JP | 5337618 B2 | 11/2013 |
| JP | 5340078 B2 | 11/2013 |
| JP | 2013228360 A | 11/2013 |
| JP | 5390578 B2 | 1/2014 |
| JP | 5425151 B2 | 2/2014 |
| JP | 5426269 B2 | 2/2014 |
| JP | 5514606 B2 | 6/2014 |
| JP | 5698010 B2 | 4/2015 |
| JP | 2015143632 A | 8/2015 |
| JP | 2016083307 A | 5/2016 |
| JP | 2016129646 A | 7/2016 |
| JP | 2016214367 A | 12/2016 |
| JP | 2017006415 A | 1/2017 |
| JP | 2017006538 A | 1/2017 |
| JP | 2017015648 A | 1/2017 |
| JP | 2017035238 A | 2/2017 |
| JP | 2017038803 A | 2/2017 |
| JP | 6123272 B2 | 5/2017 |
| JP | 6324759 B2 | 5/2018 |
| JP | 2018102597 A | 7/2018 |
| JP | 2018105622 A | 7/2018 |
| JP | 2018110717 A | 7/2018 |
| JP | 6429527 B2 | 11/2018 |
| WO | 1999008734 A1 | 2/1999 |
| WO | 1999013926 A2 | 3/1999 |
| WO | 2000032104 A1 | 6/2000 |
| WO | 2001017604 A1 | 3/2001 |
| WO | 2001017606 A1 | 3/2001 |
| WO | 2001018396 A1 | 3/2001 |
| WO | 2007110946 A1 | 10/2007 |
| WO | 2008152810 A1 | 12/2008 |
| WO | 2009082519 A1 | 7/2009 |
| WO | 2011041302 A1 | 4/2011 |
| WO | 2011080191 A1 | 7/2011 |

(56) References Cited

FOREIGN PATENT DOCUMENTS

| | | |
|---|---|---|
| WO | 2012040657 A2 | 3/2012 |
| WO | 2012139765 A1 | 10/2012 |
| WO | 2012166980 A2 | 12/2012 |
| WO | 2012126745 A2 | 2/2013 |
| WO | 2013156138 A2 | 10/2013 |
| WO | 2013180154 A1 | 12/2013 |
| WO | 2014029673 A1 | 2/2014 |
| WO | 2015023264 A1 | 2/2015 |
| WO | 2015024647 A2 | 2/2015 |
| WO | 2015082855 A1 | 6/2015 |
| WO | 2015086384 A1 | 6/2015 |
| WO | 2016048445 A1 | 3/2016 |
| WO | 2016133635 A1 | 8/2016 |
| WO | 2016198579 A1 | 12/2016 |
| WO | 2017001358 A1 | 1/2017 |
| WO | 2017218529 A1 | 12/2017 |
| WO | 2018224606 A1 | 12/2018 |

OTHER PUBLICATIONS

International Search Report and Written Opinion for International Application No. PCT/US12/40298, dated May 10, 2013.
Kolff et al., "The artificial kidney: a dialyser with a great area", 8 J. Am. Soc. Nephrology (reprinted from CXVII Acta Medica Scandinavica (Jan. 12, 1944) vol. 117(2), pp. 121-134.
Paskalev, "Georg Haas (1886-1971): The forgotten hemodialysis pioneer.", Dialysis and Transplantation, Dec. 1, 2001, vol. 30(12) pp. 828-832.
International Preliminary Report on Patentability for International Application No. PCT/US2012/040298 dated Dec. 2, 2013.
Decision on Request for Rehearing for Case IPR2016-00744, Paper 13, U.S. Pat. No. 8,092,41462, entered Sep. 26, 2016, pp. 1-8.
Determination-Reexam Ordered for Reexamination No. 901013973, U.S. Pat. No. 8,092,41462, issued Aug. 4, 2017, 13 pages total.
ISO 8638: Cardiovascular Implants and Artificial Organs—Extracorporeal Blood Circuit for Haemodialysers, Haemodiafilters and Haemofilters (Oct. 1, 2004), pp. 1-12.
Non-Final Office Action for Reexamination No. 90/013973, U.S. Pat. No. 8,092,414B2, dated Dec. 27, 2017, 27 pages total.
Patent Owner's Preliminary Response with Exhibits 2001-2008 for Case IPR2016-00744, Paper 9, U.S. Pat. No. 8,092,414B2, dated Jun. 21, 2016, 129 pages total.
Petition for Inter Partes Review Under 35 U.S.C. §§ 311-319 and 37 C.F.R. § 42.100 et. seq., Case IPR2016-00744, Paper 1, U.S. Pat. No. 8,092,414B2, submitted Mar. 11, 2016, pp. 1-67, with Exhibit 1002 (Declaration of Mr. Charles E. Clemens), pp. 1-113, 180 pages total.
Reexamination No. 90/013,973, U.S. Pat. No. 8,092,414B2, downloaded Jan. 24, 2018, 202 pages total.

\* cited by examiner

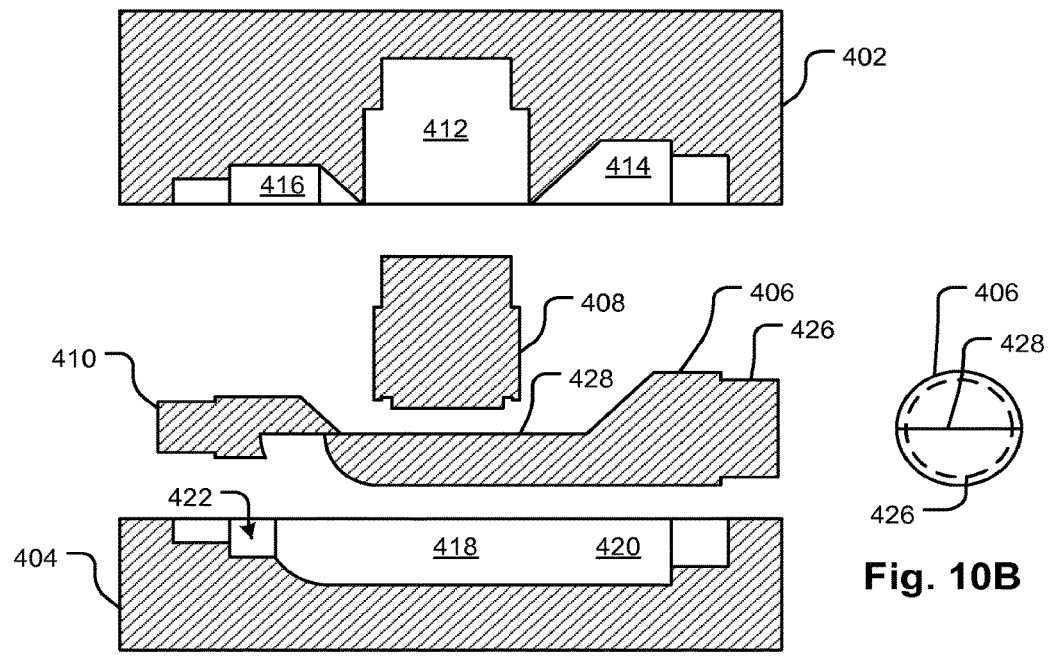
Fig. 10A
Fig. 10B
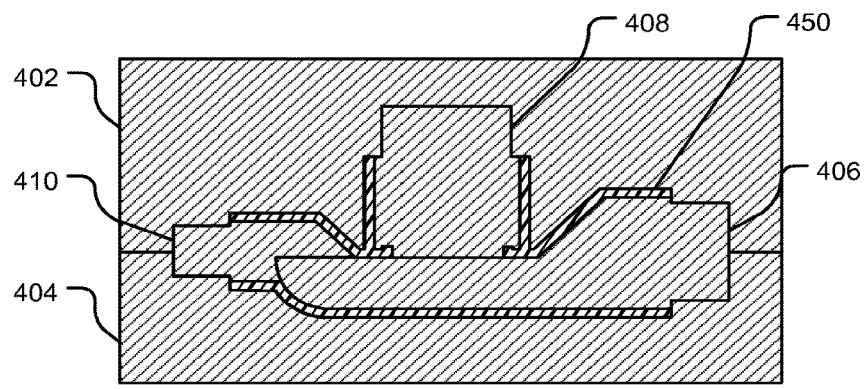
Fig. 10C

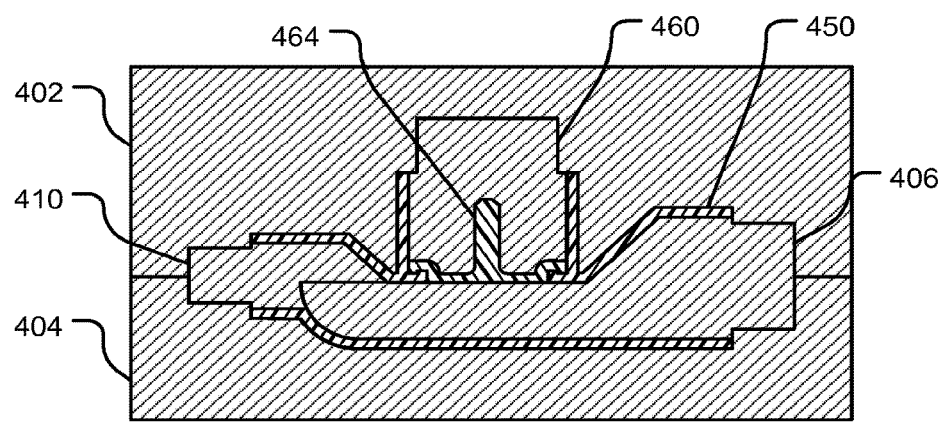
Fig. 10D
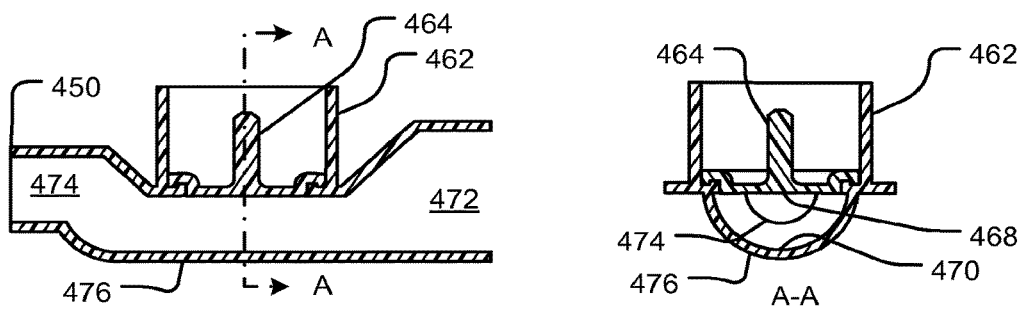
Fig. 10E
Fig. 10F
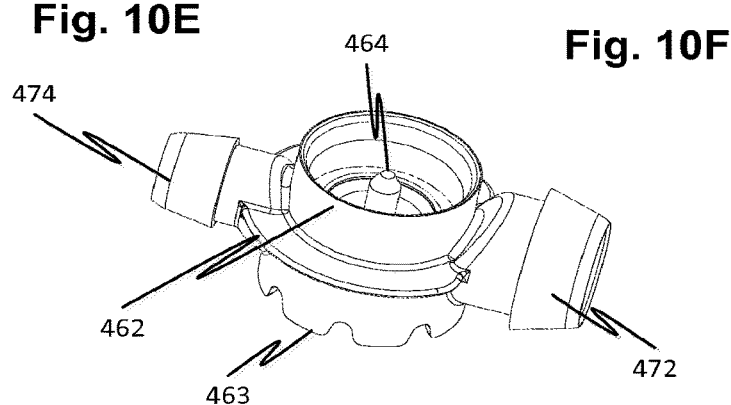
Fig. 10G

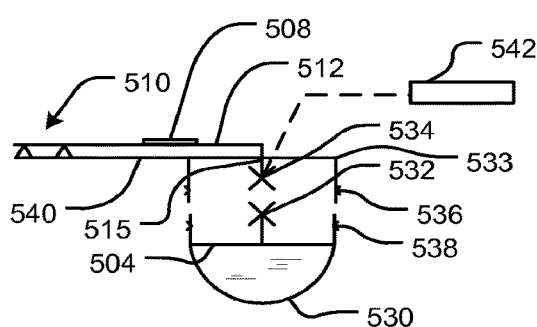
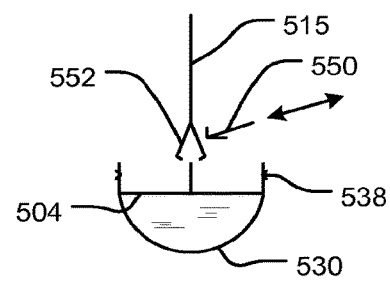
Fig. 12A        Fig. 12B
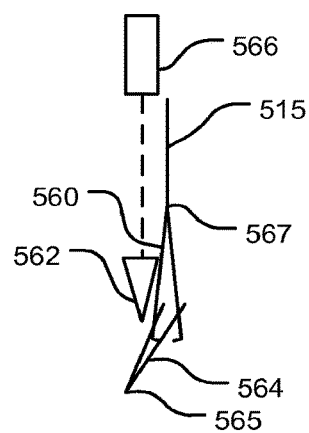
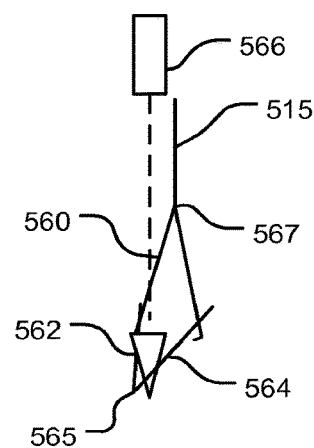
Fig. 12C        Fig. 12D

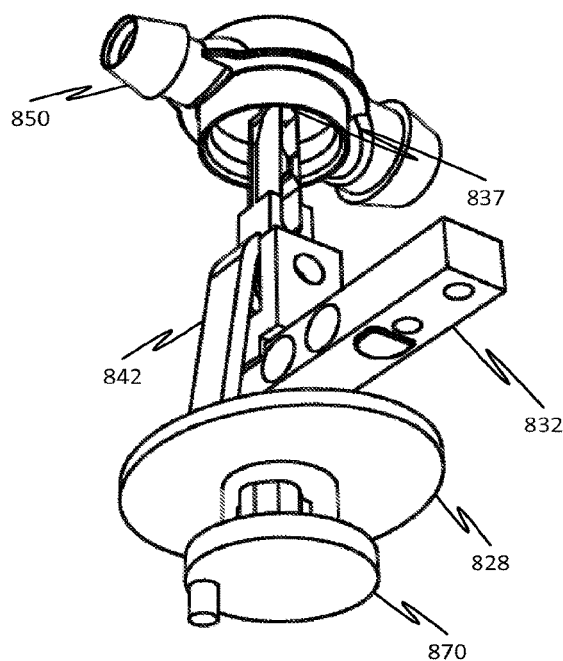
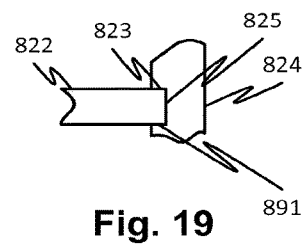
Fig. 19
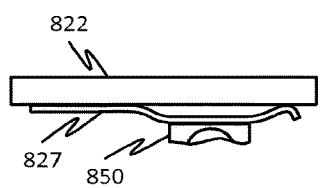
Fig. 20
Fig. 17
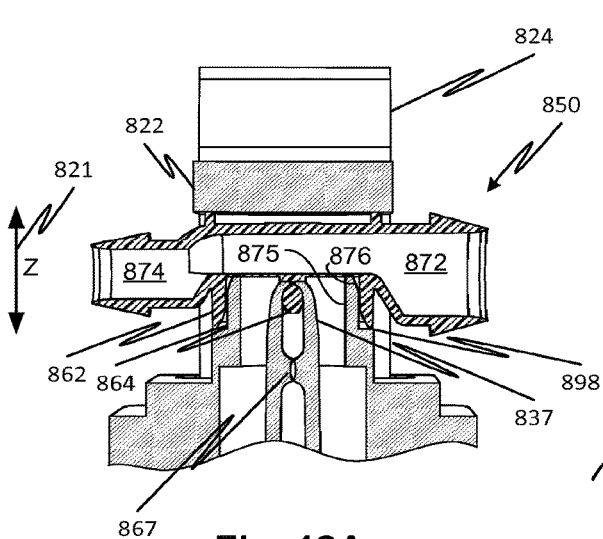
Fig. 18A
Fig. 18B
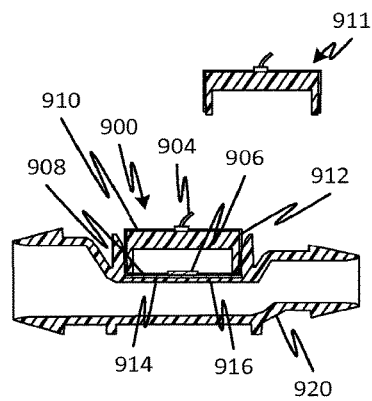
Fig. 21

US 10,345,175 B2

PRESSURE MEASUREMENT DEVICES, METHODS, AND SYSTEMS

CROSS-REFERENCE TO RELATED APPLICATIONS

The present application is a continuation of U.S. patent application Ser. No. 15/219,334 filed Jul. 26, 2016, which is a divisional of U.S. patent application Ser. No. 14/115,924 filed Nov. 6, 2013, which is a national stage entry of International Application No. PCT/US2012/040298 filed May 31, 2012, which claims the benefit of U.S. Provisional Application No. 61/544,266 filed Oct. 6, 2011 and U.S. Provisional Application No. 61/491,869 filed May 31, 2011, all of which are hereby incorporated by reference herein in their entireties.

FIELD

The disclosed subject matter relates generally to pressure measurement devices, methods, and systems and more particularly to pressure monitoring for medical applications.

BACKGROUND

FIG. 1 shows a pressure measurement pod 10 according to the prior art. In the pod 10, air chamber 45 is in communication with an air port 12 and air line 40 that can be connected to a pressure transducer (not shown). Fluid flows through a fluid chamber 60 between an inlet line 35 connected to an inlet port 70 and out of the fluid chamber 60 through an outlet port 72 into an outlet line 15. The pressure of the fluid in the fluid chamber 60 displaces a diaphragm 25 until the air chamber 45 and fluid chamber 60 are at equilibrium, which is preferably the situation when the air and fluid chambers 45 and 60 are at equal pressure.

The pod 10 is primarily made of two parts, a fluid-side shell 30 and an air-side shell 17, that, together, form an enclosure 5 that defines the fluid and air chambers 60 and 45, respectively. The ratio of the minimum to the maximum volume of the air chamber 45, including the volume of the line 40 and port 12, is proportional to the total pressure variation that can be measured by the transducer attached to the line 40. The fixed volume defined by the line 40 and port 12 serves as a limit on this ratio and therefore limits the pressure range that can be measured. Another feature of the pod 10 is that the fluid shell is such that it must be formed by a mold that has more than two parts, because of the inlet and outlet ports 70 and 72 and the recess that helps define the fluid chamber 60. Since molds with more than two parts are more expensive to design and make, this is a disadvantage.

Another feature of the pod 10 is the orientation of the inlet and outlet lines 35 and 15 owing to those of the inlet and outlet ports 70 and 72. The orientations require the pod 10 be placed in a straight run of tubing, which can make it difficult to design a compact fluid circuit assembly in which the pod is used. Yet another feature is the use of an intermediate line 40 between the transducer and the pod 10, which makes the pod assembly larger, requires more parts to be assembled, and has more seals which may fail. Another feature of prior art pods in general is the use of diaphragms that are more permeable than may be desirable. Also, the attachment between the blood side shell 30 and the air side shell 17 may be made by a compression seal (details not shown) or by another means of attachment, but in any event, may require additional steps to seal the diaphragm within.

SUMMARY

Embodiments include a method of measuring pressure, comprising: positioning on a force measuring station, a pressure pod with a diaphragm and inlet and outlet ports fluidly coupled to a chamber within the pressure pod, a first surface of the diaphragm facing the chamber to form a major part of a wall of the chamber, and a second major surface of the diaphragm facing away from the chamber and carrying a mechanical engagement feature. The force measuring station has a mechanical engagement member configured to engage with the diaphragm mechanical engagement feature, the mechanical engagement member and the diaphragm mechanical engagement feature being operable to permit the diaphragm to apply a pulling force to the mechanical engagement member, which force is in a direction tending to move the diaphragm toward the chamber upon application of a negative pressure within the chamber. The positioning is effective to permit the mechanical engagement member to access the diaphragm mechanical engagement feature. The method also comprises applying a negative pressure to the diaphragm and transmitting a force responsive thereto to the mechanical engagement member of the force measuring station; and using the force measuring station, generating a signal responsively to the force applied to the mechanical engagement element.

Embodiments also include a method of making a pressure measurement device, comprising: molding a pod body defining a chamber in a single shot molding process, the pod body including a chamber and inlet and outlet ports, the molding including forming an integral diaphragm and the inlet and outlet ports. The molding can include inserting at least one projecting mold portion, with a positive draft, which forms at least one of the inlet and outlet ports and the chamber.

Disclosed embodiments can also include a pressure measuring system, comprising: a pressure pod with a diaphragm and inlet and outlet ports fluidly coupled to a chamber within the pressure pod, a first surface of the diaphragm facing the chamber and forming a major part of a wall of the chamber and a second major surface of the diaphragm facing away from the chamber and carrying a mechanical engagement feature thereon; and a force measuring station having a mechanical engagement member configured to engage with the diaphragm mechanical engagement feature, the mechanical engagement member and the diaphragm mechanical engagement being operable to permit the diaphragm to apply a pulling force to the mechanical engagement member, which force is in a direction tending to move the diaphragm toward the chamber upon application of a negative pressure within the chamber. The force measuring station is configured to generate a signal responsively to a force applied to the mechanical engagement element.

Also included in embodiments is a pressure measurement pod for use in blood circuits, comprising: a pressure sensing pod defining a chamber, wherein the pod defines a flexible, moveable, fluid-impermeable diaphragm having a first major side thereof facing the interior of the chamber and a second major side opposite the first major side. The second major side faces outwardly away from the chamber, and the diaphragm has an engagement component configured to engage an external force measurement device from the second major side. The pod has ports on opposite sides of the chamber on the diaphragm first major side, the internal surfaces of the chamber and ports being shaped such that any contour following the surface to the outside of one of the ports traces only surfaces characterized by positive or neutral draft angles such that invasive mold portions may be withdrawn through the ports thereby permitting the pod body to be molded in a single shot molding process.

Embodiments of the disclosed subject matter further include a pressure measurement pod for use in blood circuits, comprising: a pressure sensing pod defining a chamber. The pod defines a flexible, moveable, fluid-impermeable diaphragm having a first major side thereof facing an interior of the chamber and a second major side opposite the first major side, the second major side facing outwardly away from the chamber, and the diaphragm having an engagement component configured to engage an external force measurement device from the second major side. The pod has ports on opposite sides of the chamber or the diaphragm first major side, and the chamber has a major dimension perpendicular to an axis of one of the ports that is the same or smaller than an internal dimension of one of the one of the ports.

Also included in embodiments is a pressure measurement system for use in blood circuits, comprising: a pressure sensing pod defining a chamber; and a force measurement device having a base and a force measurement member to which force is applied to generate a force signal. The pod defines a flexible, moveable, fluid-impermeable diaphragm having a first major side thereof facing an interior of the chamber and a second major side, opposite the first major side; the second major side faces outwardly away from the chamber, the diaphragm having an engagement component configured to engage the force measurement member from the second major side; the pod having a portion that forms an interference engagement with the base; and the force measurement member having a mechanical fastening mechanism configured to attach by the interference engagement with the diaphragm such that zero force is applied to the diaphragm during attachment to the diaphragm.

According to embodiments, the disclosed subject matter includes a pressure measurement device. The device has a housing with a flow channel, the housing has a single wall forming a self-supporting structure with a defined flow channel connecting two ports in communication with the flow channel. The channel has one wall portion of the housing that is substantially thinner than a remainder of the housing. The one wall portion has a major dimension that is no larger than one of the two ports, thus permitting the housing to be closed by a molding operation and without requiring the attachment of separate parts to close the housing.

The one wall portion may be circular and may constitute a diaphragm. The one wall portion may be integral with the remainder of the housing and molded in a single operation from a single quantity of material, such as medical grade thermoplastic. The one wall portion may be configured such that the flow channel housing may be closed with a single molding operation and without requiring the attachment of separate parts to close the housing. an engagement feature may be provided on the one wall portion. The engagement feature may include a protrusion. Alternatively, the engagement feature may include a ferromagnetic element or a mechanical fastener feature element. The ports may be located on opposite sides of the channel with axes that are parallel to a major plane of the one wall portion. A force transducer may be connected to the one wall portion such that displacement of the one wall portion causes displacement of the force transducer in directions corresponding to negative as well as positive pressure within the channel. A force transducer may be mechanically connected to the one wall portion such that displacement of the one wall portion causes displacement of the force transducer in directions corresponding to negative as well as positive pressure within the channel. A force transducer may be magnetically or adhesively connected to the one wall portion such that displacement of the one wall portion causes displacement of the force transducer in directions corresponding to negative as well as positive pressure within the channel.

According to embodiments, the disclosed subject matter includes a method of manufacturing a pressure measuring device. In the method, first and second major mold parts are provided which have recesses defining major parts of a housing. The method includes inserting pins in the first and second major mold parts, the pins being shaped to define a flow channel of a molded pressure measuring pod. One of the pins has a major face that defines an internal surface of a diaphragm. The method further includes closing the first and second major mold parts with the pins therebetween and injection molding a pressure pod housing and removing the pressure pod from the mold parts and withdrawing the pins from flow channel.

In embodiments, the removing may open ports in the housing that communicate through the housing. One of the pins can have a major dimension that is larger than, equal in size to, the diaphragm. One of the pins can have a major dimension that is larger than, equal in size to, a diameter of the diaphragm. The diaphragm may have an engagement feature on an outside surface thereof. The engagement feature may include a projection.

According to embodiments, the disclosed subject matter includes a pressure measuring device with a flow channel that has a diaphragm in a wall thereof, the flow channel forming a self-supporting housing with entry and exit ports providing access to an interior thereof. The diaphragm has a first engagement element on an external surface thereof and an internal surface facing said channel interior. A force transducer assembly with a second engagement element is configured to connect to the first engagement element to transmit positive negative displacement of the diaphragm to a force transducer thereof. An engagement mechanism is configured to hold the flow channel at a fixed location relative to the force transducer.

In embodiments, the force transducer may include a cantilever beam with a strain gauge thereon. The second engagement element may include a gripper that actively clamps the first engagement element and the second engagement element is connected to the force transducer. The flow channel housing may have a support surface that engages a chassis of the force transducer assembly and the force transducer assembly has a retention mechanism that holds the flow channel against the support surface. The force transducer assembly may have an actuator mechanism that opens and closes the gripper responsively to commands from a controller. The force transducer assembly may have an actuator mechanism that opens and closes the gripper responsively to commands from a controller. The force transducer assembly may have an actuator mechanism that opens and closes the gripper responsively to commands from a controller, the actuator mechanism further including a mechanism that holds the flow channel housing in place. The force transducer assembly may have an actuator mechanism that opens and closes the gripper responsively to commands from a controller, the actuator mechanism further including a mechanism that reconfigures to hold the flow channel housing in place when the gripper is closed and reconfigured to release the flow channel housing when the gripper is opened.

According to embodiments, the disclosed subject matter includes a pressure measurement pod for use in blood circuits. In the embodiment, a pressure sensing pod defines a chamber with a rigid wall portion and an integral flexible wall portion forming a flexible, moveable, fluid-impermeable diaphragm with a first major side thereof facing the interior of the chamber and a second major side opposite the first major side. The second major side faces outwardly away from the chamber, the diaphragm may have a first engagement element. The pod has ports on opposite sides of the chamber or the diaphragm first major side, the internal surfaces of the chamber and ports being shaped such that any contour following the surface to the outside of one of the ports traces only surfaces characterized by positive or neutral draft angles such that invasive mold portions may be withdrawn through the ports thereby permitting the pod body to be molded in a single shot molding process.

The diaphragm may be configured and operative to move only between and to its initial molded position and a position inward from the initial position, toward the chamber. The diaphragm may be configured and operative to move outwardly from its as-formed position and inwardly from the as-formed position. A force transducer assembly with a second engagement element may be configured to connect to the first engagement element to transmit positive negative displacement of the diaphragm to a force transducer thereof and an engagement mechanism configured to hold the pod at a fixed location relative to the force transducer. The force transducer may include a cantilever beam with a strain gauge thereon. The second engagement element may include a gripper that actively clamps the first engagement element and the second engagement element is connected to the force transducer. The pod housing may have a support surface that engages a chassis of the force transducer assembly and the force transducer assembly may have a retention mechanism that holds the pod against the support surface. The force transducer assembly may have an actuator mechanism that opens and closes the gripper responsively to commands from a controller. The force transducer assembly may have an actuator mechanism that opens and closes the gripper responsively to commands from a controller. The force transducer assembly may have an actuator mechanism that opens and closes the gripper responsively to commands from a controller, the actuator mechanism further including a mechanism that holds the pod housing in place. The force transducer assembly may have an actuator mechanism that opens and closes the gripper responsively to commands from a controller, the actuator mechanism further including a mechanism that reconfigures to hold the pod housing in place when the gripper is closed and reconfigured to release the pod housing when the gripper is opened.

Any of the foregoing devices with a gripper mechanism may employ a knife edge on the gripper that bites into a protrusion on the diaphragm or flexible wall portion.

According to embodiments, the disclosed subject matter includes a method of measuring pressure. The method includes securing a flow channel to a chassis of a measurement device. The flow channel has a flexible wall with a protrusion extending from an external surface thereof and clamping the protrusion using a gripper. The method further includes flowing a fluid through the flow channel transmitting forces caused by displacement of the flexible wall through the gripper to a force transducer. The method further includes generating electrical signals responsively to a state of the force transducer and converting the electrical signals to an indication of pressure.

The securing may include forcing the flow channel to the chassis and preventing movement of it relative to the chassis. The securing may include activating a drive single drive through a mechanical actuator to cause the clamping and the securing. The mechanical actuator may include a pair of cams. The flowing may include flowing blood. The flowing may include flowing a fluid through a first portion connected to a first port with a first cross-sectional shape that transitions to a second portion connected to a second port that may have a second cross-sectional shape, wherein the first and second cross-sectional shapes are constant or enlarge toward a respective access of the port such that the internal portion of the flow channel may be formed by pins that can be withdrawn from the flow channel after molding it. The flowing may include flowing a fluid through a first portion connected to a first port with a first cross-sectional shape that transitions to a second portion connected to a second port that may have a second cross-sectional shape, wherein the first and second cross-sectional shapes are constant or enlarge toward a respective access of the port such that the flow channel may have no more than one internal flow area expansion in either flow direction. The flow channel may be a self-supporting rigid pod structure with a fluid channel therethrough. The clamping a protrusion may include forcing a sharp edge into the protrusion. The clamping a protrusion may include forcing a sharp edge into the protrusion using a closing motion that may include no movement along an axis of the protrusion. The clamping a protrusion may include forcing a sharp edge into the protrusion using a closing motion that may include no motion that would push the protrusion in any direction.

According to embodiments, the disclosed subject matter includes a method for measuring pressure. The method includes securing a flow channel to a chassis of a measurement device, the flow channel may have a flexible wall with a first mechanical engagement feature presented from an external surface thereof. The method further includes engaging the mechanical engagement feature with a complementary engagement member connected to a force transducer and flowing a fluid through the flow channel. The method includes transmitting forces caused by displacement of the flexible wall through the complementary engagement member to the force transducer and generating electrical signals responsively to a state of the force transducer and converting the electrical signals to an indication of pressure.

The securing may include forcing the flow channel to the chassis and preventing movement of it relative to the chassis. The securing may include activating a drive single drive through a mechanical actuator to cause the engaging and the securing. The mechanical actuator may include a pair of cams. The flowing may include flowing blood. The flowing may include flowing a fluid through a first portion connected to a first port with a first cross-sectional shape that transitions to a second portion connected to a second port that may have a second cross-sectional shape, wherein the first and second cross-sectional shapes are constant or enlarge toward a respective access of the port such that the internal portion of the flow channel may be formed by pins that can be withdrawn from the flow channel after molding it. The flowing may include flowing a fluid through a first portion connected to a first port with a first cross-sectional shape that transitions to a second portion connected to a second port that may have a second cross-sectional shape, wherein the first and second cross-sectional shapes are constant or enlarge toward a respective access of the port such that the flow channel may have no more than one internal flow area expansion in either flow direction. The flow channel may be a self-supporting rigid pod structure with a fluid channel therethrough. The engaging may include clamping the mechanical engagement feature. The mechanical engagement feature may include a protrusion. The engaging may include using a motion that may include no urging of the mechanical engagement element.

According to embodiments, the disclosed subject matter includes a system for measuring pressure in a fluid circuit. A flow channel has a housing with first and second ports connected by an internal flow path. A force measuring apparatus has an engagement portion to which the flow channel is securely attachable and against which the flow channel is immobilized. A retention mechanism is configured to hold the flow channel housing against the engagement portion to maintain a desired position thereof relative to the force measuring apparatus. The internal flow path is defined in part by a flexible wall portion that is mechanically engaged with the force measuring member of the force measuring apparatus, the force measuring apparatus is configured to generate a force indicating signal responsively to displacement of the force measuring member resulting from displacement of the flexible wall portion. The flexible wall portion is configured to present a smooth internal surface to the internal flow path. The internal flow path extends between the access of each port has a hydraulic diameter of no more than 15 mm at all points therethrough.

The internal flow path may have a cross-section whose aspect ratio does not exceed 3. The housing may be a self-supporting inline pod structure. The internal surface of the flow path may have a positive or neutral draft from any point toward at least one of the first and second ports and at all of said internal surface from said any one point to said at least one of the first and second ports. The flexible wall portion may have a smooth sided protrusion that engages with the force measuring apparatus. The force measuring apparatus may have a gripper mechanism that grips the protrusion. The protrusion may have a portion with a uniform cross-section and the force measuring apparatus gripper mechanism has a claw-like end that is configured to close around the protrusion without any position-selection bias along an axis of the protrusion such that the claw remains engaged with the protrusion at a point where it initially contacts the protrusion. The flow channel housing, including the flexible wall portion and protrusion, may be integral and of the same material such that they are configured to be molded as a single element. One of the ports may be larger than the other. The larger of the first and second ports may be connected to a fluid circuit for medical treatment and the larger of the ports is connected to a pump tubing segment and the other is connected to a non-pump tubing segment. The maximum internal dimension at any point of the flow path may be limited to as little as 10 mm. The force measuring apparatus may be configured to verify the position or force with which the flow channel housing is engaged with the engagement portion. The internal flow path may have a cross-section whose aspect ratio does not exceed 3. The flexible wall portion can have a surface facing away from the internal flow path which has at all points thereof a positive or neutral draft such that its outer surface can be molded, along with the outer surface of the rest of the housing, by a two part mold. The maximum dimension of the internal flow path can be limited to vary within the range of 5 to 10 mm. The housing may have an annular rim and the force measuring apparatus has a boss configured to mate with the annular rim.

The flexible wall portion may be a diaphragm and the retention mechanism, housing, and engagement portion may be configured to immobilize the perimeter of the diaphragm with respect to the force measuring member to minimize displacement of the diaphragm.

According to embodiments, the disclosed subject matter includes a method for measuring pressure, comprising: securing a flow channel to a chassis of a measurement device, the flow channel has a flexible wall with a first mechanical engagement feature presented from an external surface thereof. The method further includes engaging the mechanical engagement feature with a complementary engagement member connected to a force transducer. The securing is effective to immobilize the flow channel relative to the force transducer. The method further includes detecting at least one of the position and orientation of the of the flow channel relative to transducer and comparing to at least one of a predefined position and orientation, and generating a signal responsive to the detecting, and flowing a fluid through the flow channel. The method includes transmitting forces caused by displacement of the flexible wall through the complementary engagement member to the force transducer and generating electrical signals responsively to a state of the force transducer and converting the electrical signals to an indication of pressure.

The securing may include forcing the flow channel to the chassis and preventing movement of it relative to the chassis. The securing may include activating a drive single drive through a mechanical actuator to cause the engaging and the securing.

The mechanical actuator may include a pair of cams. The flowing may include flowing blood. The flowing may include flowing a fluid through a first portion connected to a first port with a first cross-sectional shape that transitions to a second portion connected to a second port that has a second cross-sectional shape, wherein the first and second cross-sectional shapes are constant or enlarge toward a respective access of the port such that the internal portion of the flow channel may be formed by pins that can be withdrawn from the flow channel after molding it. The flowing may include flowing a fluid through a first portion connected to a first port with a first cross-sectional shape that transitions to a second portion connected to a second port that has a second cross-sectional shape, wherein the first and second cross-sectional shapes are constant or enlarge toward a respective access of the port such that the flow channel has no more than one internal flow area expansion in either flow direction. The flow channel may be a self-supporting rigid pod structure with a fluid channel therethrough. The engaging may include clamping the mechanical engagement feature. The mechanical engagement feature may include a protrusion. The engaging may include using a motion that may include no urging of the mechanical engagement element.

According to embodiments, the disclosed subject matter includes a method of measuring pressure, including positioning on a force measuring station, a pressure pod with a diaphragm and inlet and outlet ports fluidly coupled to a chamber within the pressure pod, a first surface of the diaphragm facing the chamber to form a major part of a wall of the chamber, and a second major surface of the diaphragm facing away from the chamber and carrying a mechanical engagement feature. The force measuring station has a mechanical engagement member configured to engage with the diaphragm mechanical engagement feature, the mechanical engagement member and the diaphragm mechanical engagement feature is operable to permit the diaphragm to apply a pulling force to the mechanical engagement member, which force is in a direction tending to move the diaphragm toward the chamber upon application of a negative pressure within the chamber. The positioning is effective to permit the mechanical engagement member to access the diaphragm mechanical engagement feature. The method includes applying a negative pressure to the diaphragm and transmitting a force responsive thereto to the mechanical engagement member of the force measuring station. The method includes using the force measuring station, generating a signal responsively to the force applied to the mechanical engagement element. The chamber may have a hemicylindrical shape whose wall flows smoothly into a full cylindrical shape of one of the inlet and outlet ports. The method may include detecting the positioning, and responsively to the detecting, activating an engagement actuator to bring the mechanical engagement member into engagement with the diaphragm mechanical engagement feature. Engagement between the mechanical engagement member of the force measuring station and the diaphragm mechanical engagement feature may be by one of an adhesive between the member and the feature and a mechanical coupling.

According to embodiments, the disclosed subject matter includes a method of making a pressure measurement device including molding a pod body defining a chamber in a single shot molding process, the pod body may include a chamber and inlet and outlet ports, the molding may include forming an integral diaphragm and the inlet and outlet ports. The molding includes inserting at least one projecting mold portion, with a positive draft, which forms at least one of the inlet and outlet ports and the chamber.

The molding may include inserting two of said projecting mold portions to form respective inlet and outlet ports and the chamber, the outlet port has a greater maximum diameter than the inlet port. The method may include molding a diaphragm to said pod body by way of a projecting mold portion. The projecting mold portions may be pins, each of said pins is of different shapes.

According to embodiments, the disclosed subject matter includes a pressure measuring system including a pressure pod with a diaphragm and inlet and outlet ports fluidly coupled to a chamber within the pressure pod, a first surface of the diaphragm facing the chamber and forming a major part of a wall of the chamber and a second major surface of the diaphragm facing away from the chamber and carrying a mechanical engagement feature thereon. A force measuring station has a mechanical engagement member configured to engage with the diaphragm mechanical engagement feature, the mechanical engagement member and the diaphragm mechanical engagement is operable to permit the diaphragm to apply a pulling force to the mechanical engagement member, which force is in a direction tending to move the diaphragm toward the chamber upon application of a negative pressure within the chamber. The force measuring station is configured to generate a signal responsively to a force applied to the mechanical engagement element. The chamber has a hemicylindrical shape whose wall flows smoothly into a full cylindrical shape of one of the inlet and outlet ports.

According to embodiments, the disclosed subject matter includes a pressure measurement pod for use in blood circuits with a pressure sensing pod defining a chamber. The pod defines a flexible, moveable, fluid-impermeable diaphragm has a first major side thereof facing the interior of the chamber and a second major side opposite the first major side. The second major side faces outwardly away from the chamber, the diaphragm has an engagement component configured to engage an external force measurement device from the second major side. The pod has ports on opposite sides of the chamber or the diaphragm first major side, the internal surfaces of the chamber and ports is shaped such that any contour following the surface to the outside of one of the ports traces only surfaces characterized by positive or neutral draft angles such that invasive mold portions may be withdrawn through the ports thereby permitting the pod body to be molded in a single shot molding process. The diaphragm may be configured and operative to move only between and to its initial molded position and a position inward from the initial position, toward the chamber. The diaphragm may be configured and operative to move outwardly from its as-formed position and inwardly from the as-formed position.

According to embodiments, the disclosed subject matter includes a pressure measurement pod for use in blood circuits including a pressure sensing pod defining a chamber. The pod defines a flexible, moveable, fluid-impermeable diaphragm has a first major side thereof facing an interior of the chamber and a second major side opposite the first major side. The second major side faces outwardly away from the chamber, the diaphragm has an engagement component configured to engage an external force measurement device from the second major side. The pod has ports on opposite sides of the chamber or the diaphragm first major side, the chamber has a major dimension perpendicular to an axis of one of the ports that is the same or smaller than an internal dimension of one of the one of the ports. The chamber may have a cylindrical interior surface. The engagement component may include at least one of a projection integral with the diaphragm, a magnet, a ferromagnetic material or member, a Velcro fastener, a hook, an eye, a threaded recess, a threaded projection, a blade lock, a snap, and a surface with an adhesive face. The engagement component may include a fastener.

Objects and advantages of embodiments of the disclosed subject matter will become apparent from the following description when considered in conjunction with the accompanying drawings.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIG. 10A shows an exploded section view of a mold assembly for fabricating a pressure pod according to an embodiment of the disclosed subject matter.

FIG. 10B shows an end view of a pin portion of the mold assembly of FIG. 10A according to embodiments of the disclosed subject matter.

FIG. 10C shows the mold assembly of FIG. 10A configured for molding a pressure measuring pod during a first molding shot according to embodiments of the disclosed subject matter.

FIG. 10D shows the mold assembly of FIG. 10B modified by a mold portion for making a diaphragm during a second molding shot according to embodiments of the disclosed subject matter.

FIGS. 10E and 10F shows a pressure pod result of the two-shot molding process in lateral and axial section views according to embodiments of the disclosed subject matter.

FIG. 10G shows a pressure pod according to embodiments of the disclosed subject matter.

FIG. 12A is a schematic diagram of a pressure pod and force measurement assembly according to embodiments of the disclosed subject matter.

FIG. 12B is a schematic diagram of a pressure pod and force measurement assembly showing a mechanism for placing a jaw-type attachment mechanism in a receptive state according to embodiments of the disclosed subject matter.

FIGS. 12C and 12D are schematic diagrams of a force measurement assembly showing an alternative mechanism for placing a jaw-type attachment mechanism in an operational state and a receptive state, respectively, according to embodiments of the disclosed subject matter.

FIG. 17 shows internal details of the assembly of FIG. 16.

FIG. 18A shows the assembly of FIG. 16 in partial cross section.

FIG. 18B shows a feature of an engagement component of a force transducer.

FIG. 19 shows a feature that may be used in the embodiment of FIGS. 16 through 18.

FIG. 20 shows a feature of a mechanism that may be used in the disclosed embodiments for generating a constant urging force pushing the pod against a seat of a pressure detection mechanism.

FIG. 21 illustrates an embodiment of a pressure pod in which a strain gauge is attached directly to the diaphragm and an electrical connector connects leads to and from a driver circuit for reading pressure signals to form an embodiment that may be included as part of a disposable circuit.

DETAILED DESCRIPTION

Figure 1:
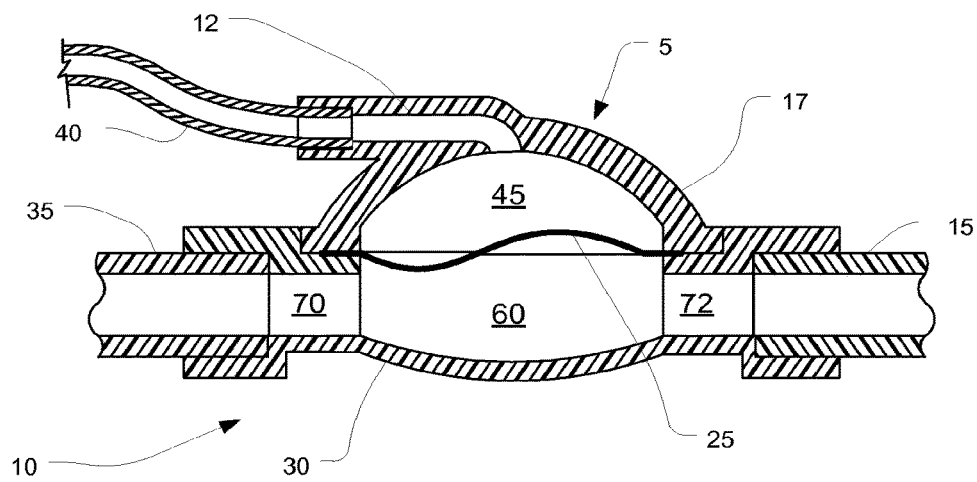
FIG. 1 shows a cross section of a pressure measuring pod according to the prior art.
Figure 2:
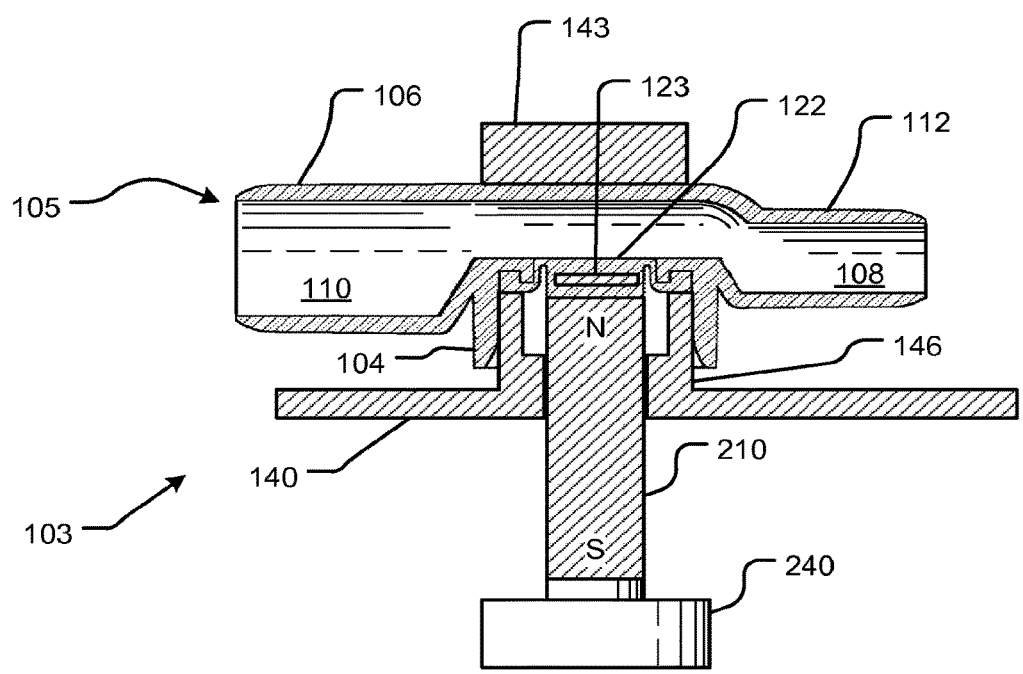
FIG. 2 shows a pressure measurement device according to disclosed embodiments.

Referring to FIG. 2, a pressure measurement device 103 has a flow or fluid circuit portion 105 with a first port 106 and a second port 112. In the present embodiment, the first port 106 is larger to accommodate a larger tube in an embodiment where the pressure measurement device 103 is to be directly connected to a pump tube portion (see, e.g., FIG. 9). The second port 112 is for connection to a smaller diameter tube. A diaphragm 122 has a magnet or ferromagnetic material 123 embedded within it. The diaphragm seals a portion of a continuous lumen spanning between 110 and 108 with a cross-sectional area that is substantially uniform to reduce the risk of dead zones that can cause clotting when the device 103 is used for measuring blood pressure. Alternatively, the cross section may vary as a result of the positive draft angles used to allow the mold pins to be removed so that there is a narrowing from one port toward the center of the pod and then a widening of the cross section on the way to the opening of the other port. It is possible for the pins to be shaped such that the flow area is largest in the middle despite the positive draft angles, but certain benefits accrue where the area changes little, including the reduction in turbulence otherwise caused by flow deceleration. Note that flow area inserts may be used to adapt tubes to the ports so that the requirements of the beneficial molding process described herein do not have to constrain choices for connecting tubes to the pod. A receptacle 104 receives a mating guide portion 146 extending from the body of a blood treatment machine or a chassis of a transducer mechanism 140. The components 104 and 146 cooperate to position the fluid circuit portion 105 with respect to a magnet 210 which in turn is positioned with respect to a load cell 240. The diaphragm 122 exerts pressure or pulls on the magnet 210, depending on the pressure in the lumen, which in turn exerts a positive or negative force on the load cell 240. A retention device, such as a bar 143 may be employed to hold the pod 105 against the mating guide portion 146 and may be provided with a suitable mechanism for engaging and disengaging. Element 104, which forms an annular rim, may seat against the chassis of the transducer 140 directly or, as shown, the mating guide portion (or annular boss) may seat against the pod at an interference interface indicated at 147 thereby immobilizing the pod housing. With the retention bar 143 or equivalent mechanism, the engagement is suitable for immobilizing the support of the diaphragm and helping to ensure accurate measurement with a diaphragm having lower compliance than would attend the use of a corrugated diaphragm (See FIG. 24C infra).

Figure 3:
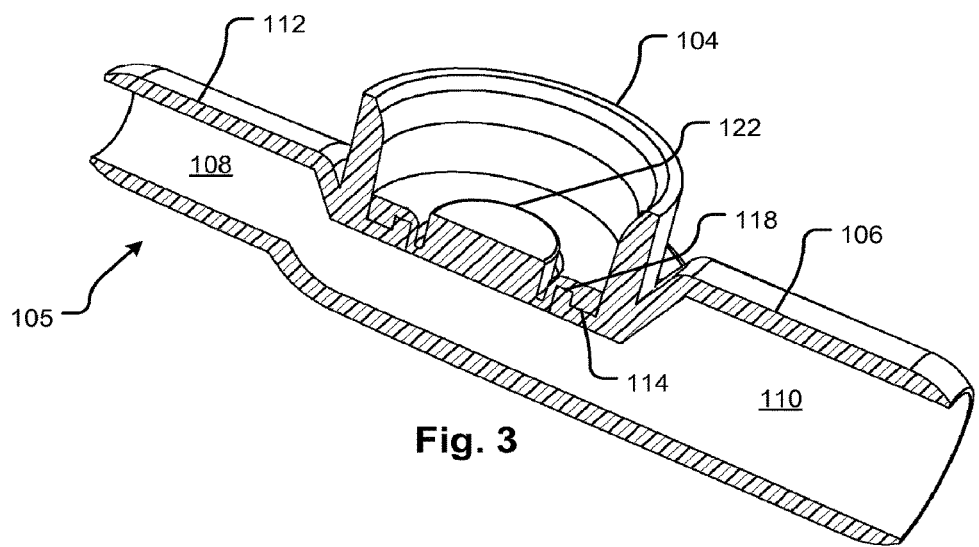
FIG. 3 shows a cross section of a fluid circuit portion of a pressure measuring device according to a variant of the embodiment of FIG. 2.

FIG. 3 shows the fluid circuit portion 105 according to a different embodiment in which the diaphragm 122 is formed of a flexible material that is magnetic. For example, the diaphragm 122 may be formed of a flexible polymer with embedded ferromagnetic particles. The diaphragm 122 may be magnetized or unmagnetized. Also shown in FIG. 3 are interlocking flutes 114 and 118 that can aid in the creation of a durable seal. Other components of the device of FIG. 3 are labeled with the same numerals as used in the prior figure so they will not be described again.

Figure 4A:
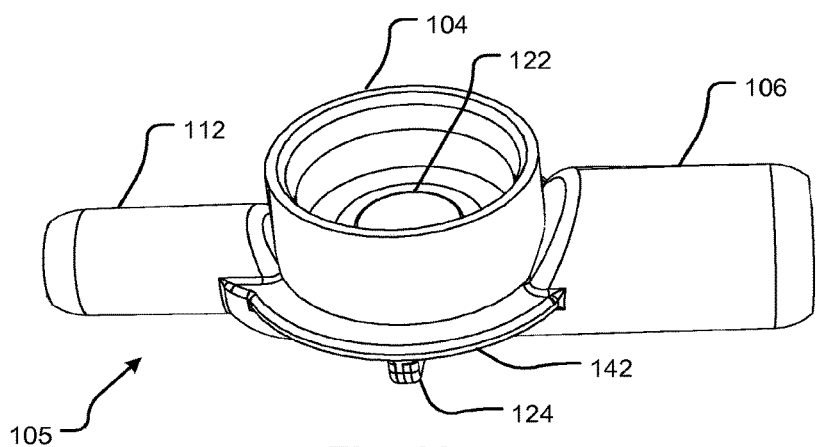
FIGS. 4A and 4B show respective views of the embodiment of FIG. 3.
Figure 4B:
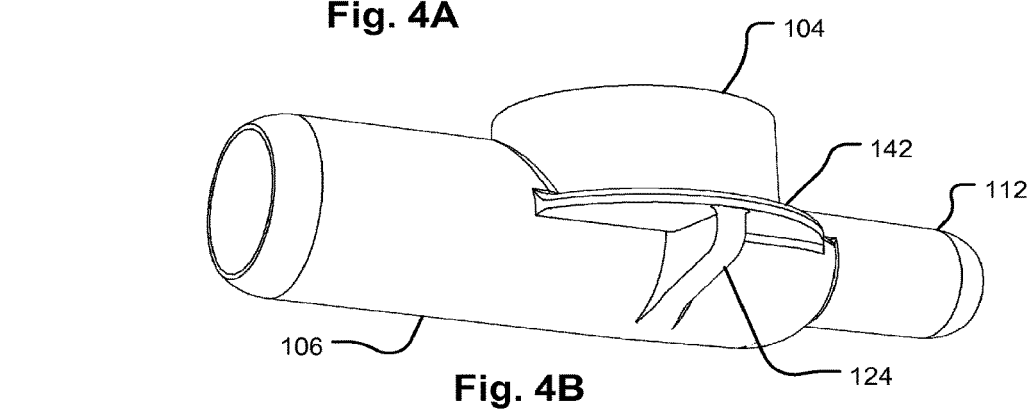

FIGS. 4A and 4B show the embodiments of FIG. 2 or 3 from two sides. A support rim 142 and a buttress 124 feature are shown. Other components of the device of FIGS. 4A and 4B are labeled with the same numerals as used in the prior figures so they will not be described again.

Figure 5:
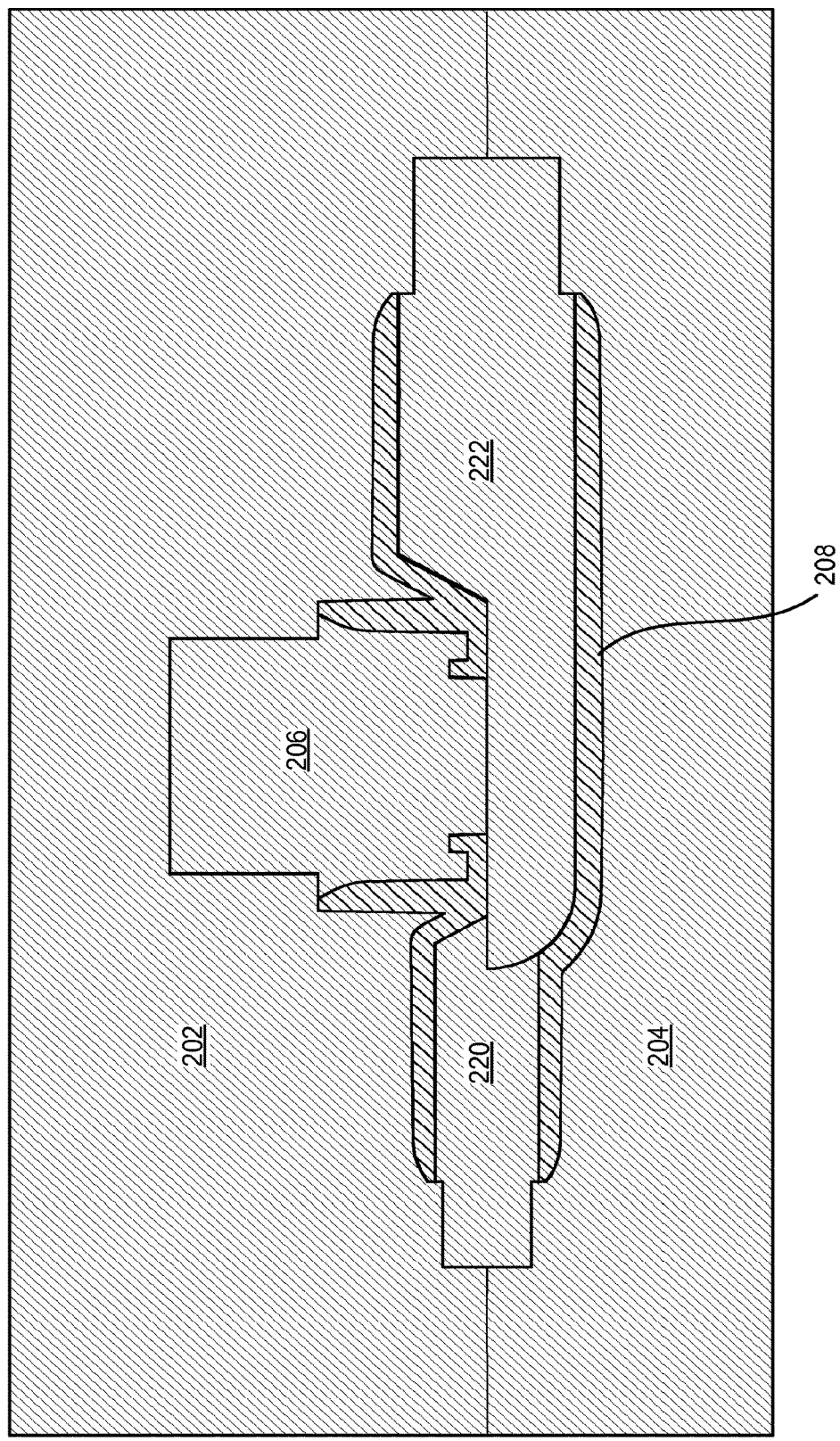
FIGS. 5 and 6 show cross sections of stages in the molding of the embodiment of FIG. 3.
Figure 6:
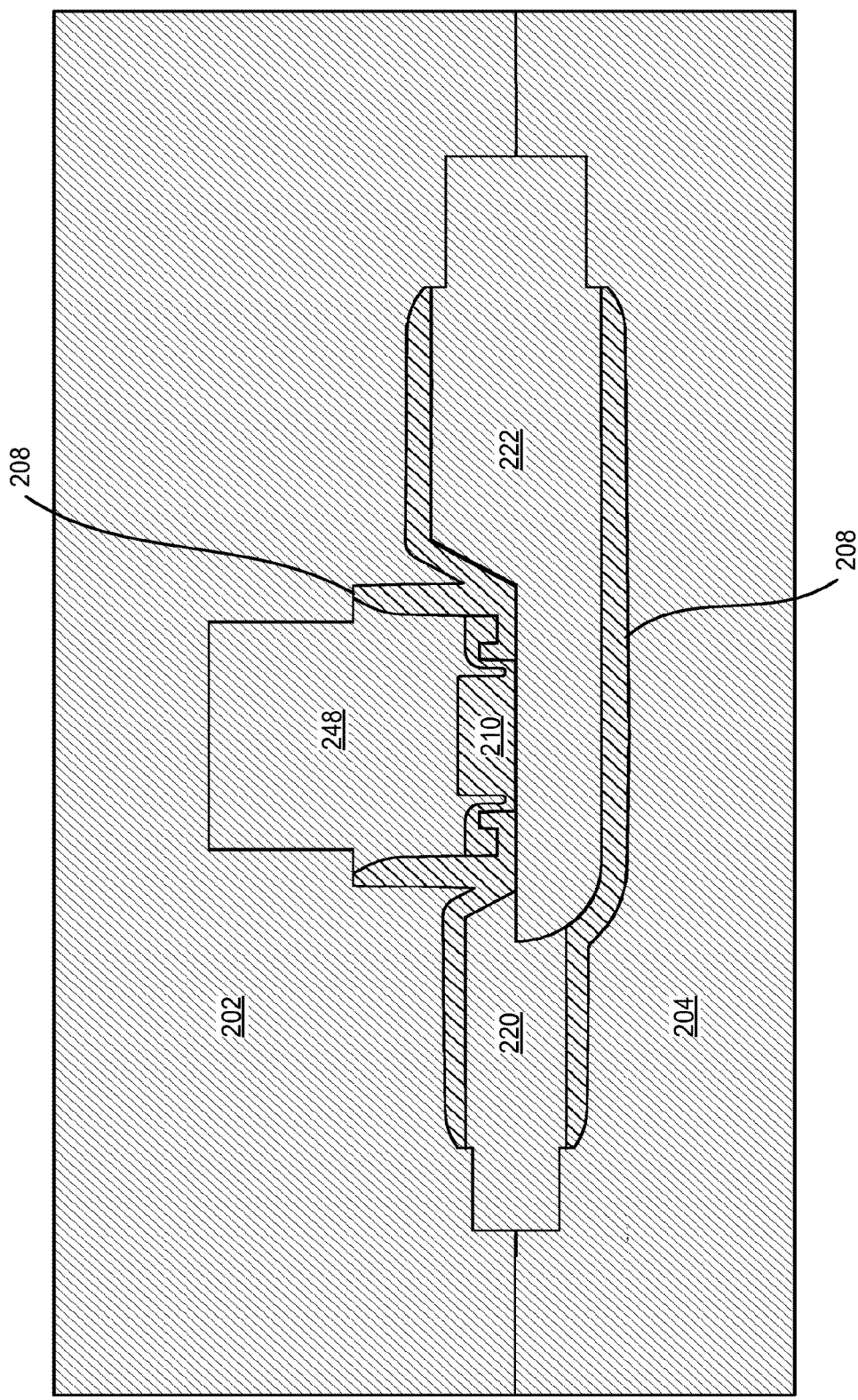

FIGS. 5 and 6 show stages in the manufacture of fluid circuit portion 105. In FIG. 5, upper and lower molds 202 and 204 and pins 206, 222, and 220 cooperatively define a hollow which when filled with a polymer material 208 form the body of the fluid circuit portion 105. As shown in FIG. 6, pin 206 is removed and replaced with a pin 248 which defines a space which when filled with polymer material 210 forms the diaphragm 122. In the latter operation, the polymer forming the body 105 forms part of the mold for the diaphragm and therefore the polymer for the body may be chosen from materials with a higher melting point than that used for the diaphragm 122. Alternatively a curable polymer may be employed. The shapes of the pins may vary from what is shown according to the characteristics of the molding process.

Figure 7:
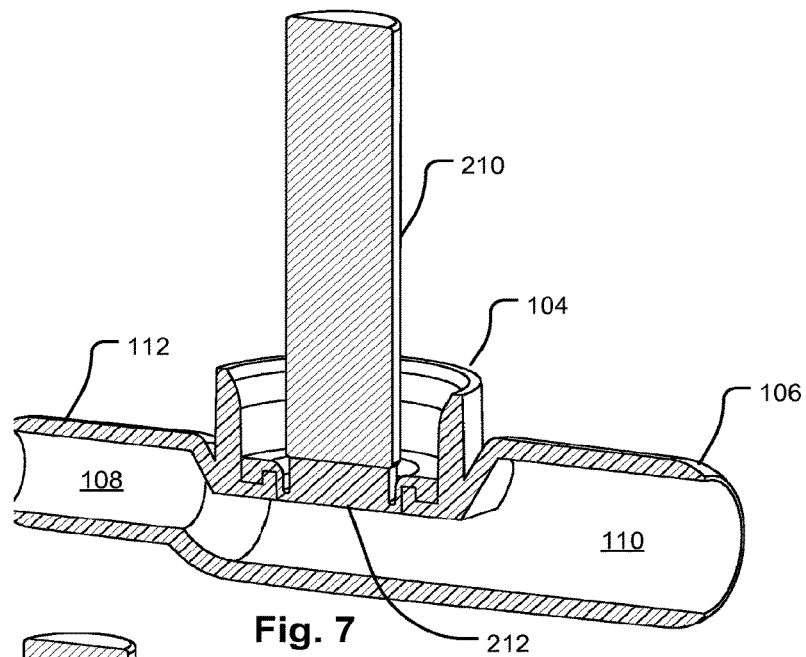
FIG. 7 shows a section of the flow circuit portion of a variant the embodiment of FIG. 2 in relation to a magnet component.
Figure 8:
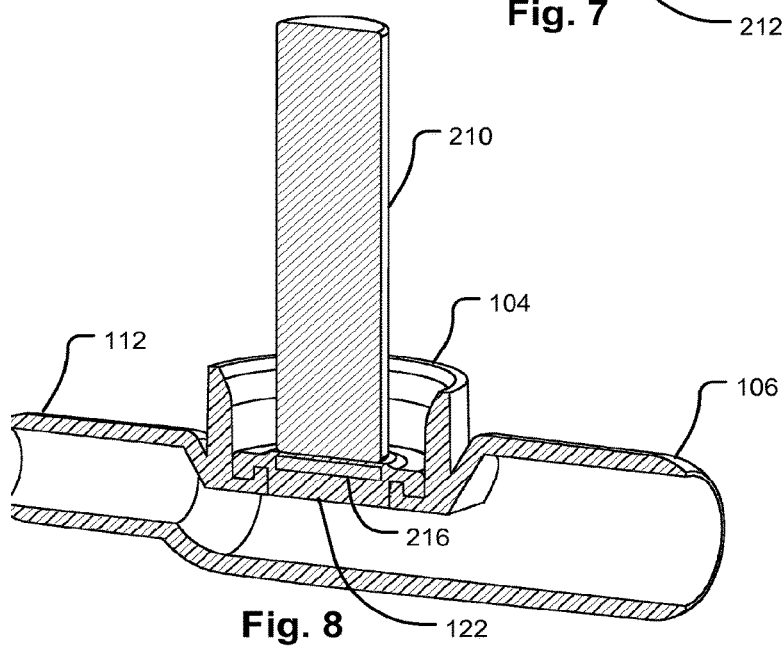
FIG. 8 shows a section of the flow circuit portion of the embodiment of FIG. 2 in relation to a magnet component.

FIGS. 7 and 8 show cross sections of the fluid circuit portion 205 with a magnetic diaphragm 212 and a diaphragm 122 with an embedded magnetic element 216, respectively. Other components of the device of FIGS. 7 and 8 are labeled with the same numerals as used in the prior figure so they will not be described again.

Figure 9:
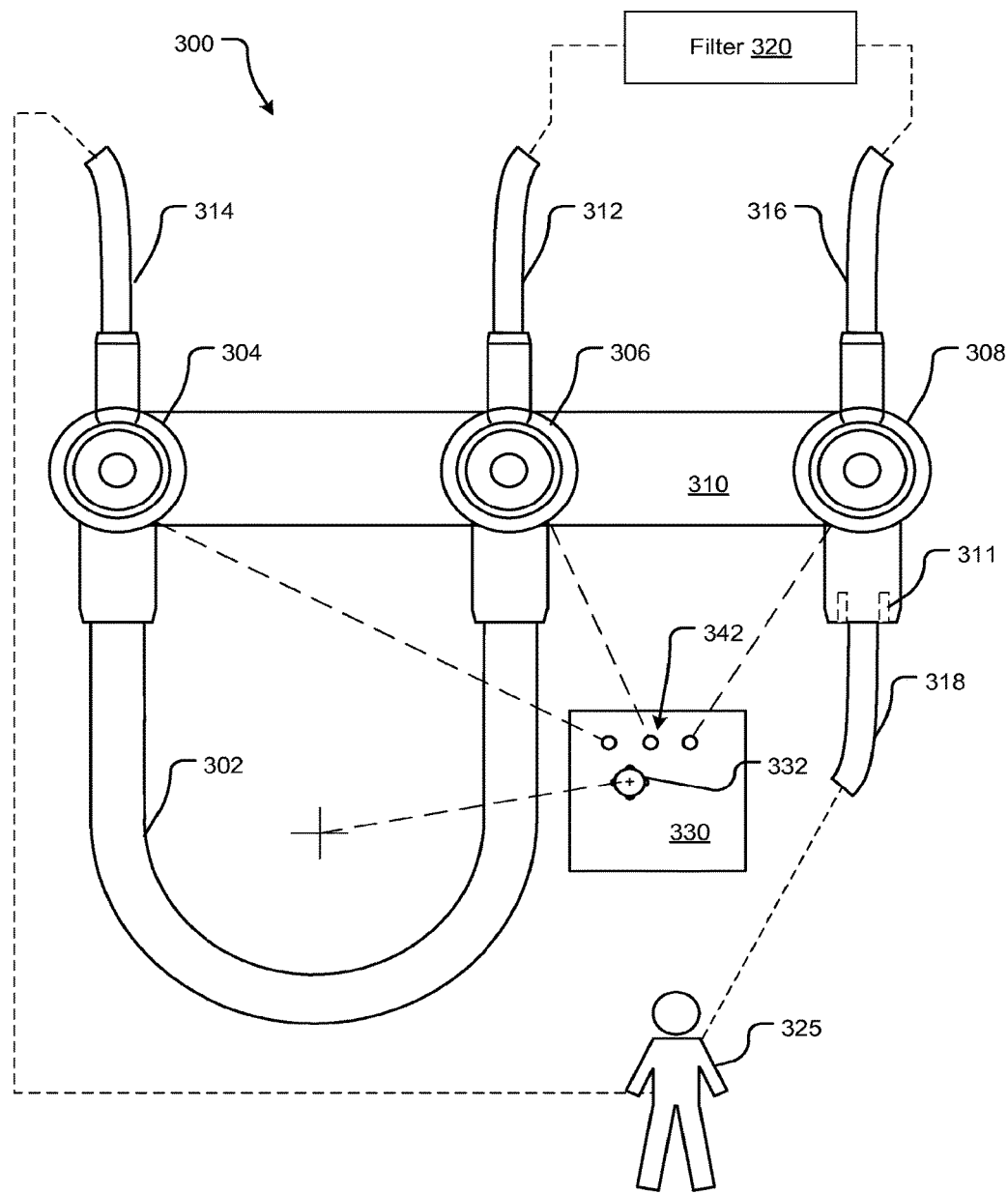
FIG. 9 shows a flow circuit component incorporating flow circuit portions of the pressure measurement devices according to embodiments as shown and/or described herein.

FIG. 9 shows a fluid circuit 300 with three pressure pods (fluid circuit portions as is 105) 304, 306, and 308 attached together by a single frame 310. A pumping portion 302 and arterial blood line 314 and venous blood line 318, and pre- and post-filter lines 312 and 316 to and from filter 320, respectively, can be pre-attached so that the components can all be simultaneously positioned and attached to a treatment machine 330. This attachment may simultaneously register the pods 304, 306, and 308 with transducer fixtures 342 and a peristaltic pump actuator 332. The connections between arterial 314 and venous 318 blood lines are shown figuratively as is a patient 325. An adapter 311 may be provided to allow connection of small diameter tubes as required, in embodiments in which the pod chamber is the same size as one of the pins used to mold the pod.

FIGS. 10A and 10B show components for fabricating a pressure pod according to embodiments of the disclosed subject matter. FIGS. 10C and 10D show stages in the manufacture of a pressure pod according to embodiments of the disclosed subject matter.

In FIGS. 10A and 10B, pins 406, 408, and 410 and upper and lower molds 402 and 404 cooperatively define a hollow, which, when filled with a polymer material, for example, form the body 450 of the pressure pod. Recesses 412, 414, and 416 in upper mold 402 mate with respective portions of pin 410, pin 408, and pin 406 (i.e., projecting mold portions), and recesses 418, 420, and 422 in lower mold 404 mate with respective portions of pin 410, pin 408, and pin 406.

As can be seen from FIGS. 10A and 10B, each of pins 406 and 410 can have outer end portions that have respective diameters less than maximum diameters thereof. Further, pin 406 can have a "halved" portion 428 that bisects the pin 406 horizontally in end view. Thus, one part of pin 406 can form a "full" cylinder portion of a flow or fluid circuit portion, and the flow/fluid circuit can transition gradually—such that the flow/fluid channel has a reduced, insignificant amount of dead space or lacks dead space, for example—to a half-cylinder portion formed by portion 428.

FIGS. 10C and 10D show that the pressure pod can be formed in a two-stage process. As shown in FIG. 10D, pin 408 from FIG. 10C is removed and replaced with pin 460 that defines a space, which, when filled with polymer material forms a diaphragm within a receptacle 462 of the pressure pod. FIG. 10D shows that the diaphragm can have a mechanical engagement feature 464. As will be discussed in more detail later, mechanical engagement feature 464 can be engaged by a mechanical engagement member, such as a gripper, of a pressure sensing or measuring apparatus. The engagement feature 464, when engaged, can be configured and operative to cause movement of the mechanical engagement member responsively to pressure variations due to fluid flow within the flow/fluid channel of the pressure sensing pod. The pod or the device used to hold the pod firmly seated for engagement with the force transducer device, may employ a spring to generate a consistent urging force. The pod of FIG. 10G has a crenelated edge, indicated at 463, which may provide a spring-like effect for this purpose in conjunction with a precise hold down latch mechanism, for example, the retention bar 824 of FIGS. 16 to 18.

Alternatively, the pressure pod can be formed in a one-stage or single-shot process. In such a case, internal surfaces of the chamber and ports of the pressure pod can be shaped such that any contour following the surface to the outside of one of the ports traces only surfaces characterized by positive or neutral draft angles such that invasive mold portions or projecting portions (e.g., pins 406, 460, and 410) may be withdrawn through the ports thereby permitting the pod body to be molded in the single shot molding process.

In single-shot or one-stage molding, the diaphragm can be formed in one-piece with the body of the pod 450 so as to have a chamber formed by wall 476 and inlet and outlet ports 472, 474. That is to say, the single molding stage can include forming an integral diaphragm with the inlet and outlet ports 472, 474, for instance.

Though FIGS. 10A, 10B, 10C, and 10D show three pins per step, three pins is not a requirement. For instance, each of the pins can be halved vertically to double the number of pins. Additionally, the pins and recesses can have different dimensions or geometries (e.g., diameters, oval rather than circular, etc.) than as shown in FIGS. 10A, 10B, and 10C. Alternatively, less than three pins may be used, for example, two.

FIGS. 10E and 10F show a pressure pod result of the two-shot molding process in lateral and axial section views, respectively, according to embodiments of the disclosed subject matter. A pressure pod made using a single-shot process would look similarly, except the diaphragm can be integral to or formed in one piece with the body of the pod 450. Thus, an interlocking step portion, as shown in FIGS. 10E and 10F for the two-shot process may be omitted.

In either case, a pressure pod made via the one-shot or two-shot processes can have a fluid chamber with a hemicylindrical shaped wall portion 476 whose wall can flow smoothly into a full cylindrical shape of the inlet port 472 and/or the outlet port 474. An inner surface 470 of the fluid chamber coincides with port 472, which can be a pump tubing port, and can be characterized by positive or neutral draft angles such that invasive mold portion 406 may be withdrawn. Wall 468, which can include a first major surface of the diaphragm, can form a base or flat portion of the hemicylinder. Such configuration of the pressure pod fluid chamber can create an internal volume thereof that reduces any fluid "dead" spots or space.

An inner wall construction of the pressure pod defining an internal volume may be constructed differently than shown in FIGS. 10E, 10F, and 10G, for example, with differently sized, differently shaped, and different numbers of fluid flow portions. For instance, though FIGS. 10E, 10F, and 10G show port 472 having a larger inlet diameter than that of port 474, the sizes can be different than shown, such as the same size or reversed in size. Thus, in embodiments, neither of the ports may be connected to a pump tubing port and can instead be positioned at another portion of a fluid circuit where the tubing sizes are the same, for instance.

FIG. 10G shows a pressure pod according to embodiments of the disclosed subject matter, with differently configured inlet and outlet ports 472, 474, whereby these ports each have tubing retaining features to facilitate sealing between and retention of tubing fitted over the ports. Other tube retaining features may be employed optionally or alternatively, such as clamps.

Though FIGS. 10E, 10F, and 10G show engagement feature 464 as a nipple- or rod-shaped protrusion, embodiments are not limited to such construction. For instance, engagement feature 464 can be formed as a loop, as a hoop, in a T-shape, in a Y-shape, or as a bulb, for instance. Further, as shown in FIG. 11C, the engagement feature of the diaphragm may be a recess 526. Of course, like engagement feature 464 mentioned above, recesses according to embodiments are not limited in shape and geometry to the configuration shown in FIG. 11C.

Additionally, any embodiments of the diaphragm can have flexibility promoting portions, such as groove or grooves 528 shown in FIG. 11C. Optionally, embodiments of the diaphragm can have governor portions, whereby certain flexure of the diaphragm is limited or prevented. Further, the diaphragm itself can be in a form other than what is explicitly shown in the figures. For instance, diaphragms according to embodiments of the disclosed subject matter can have concave or convex faces facing inward to the inner volume of the pressure pod.

Figure 11A:
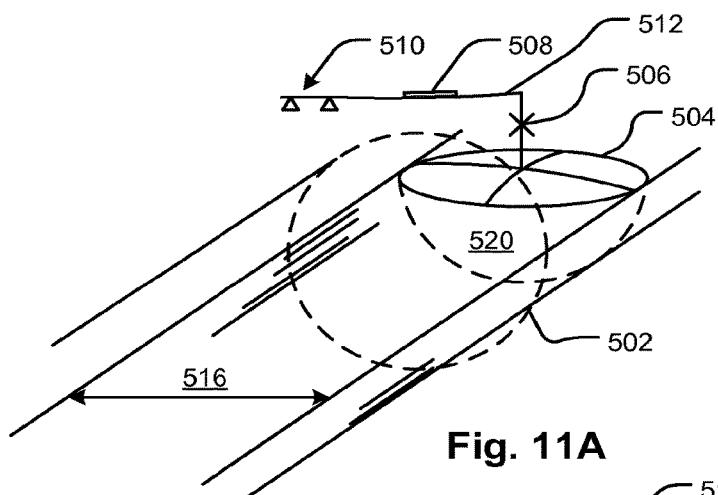
FIGS. 11A and 11B show schematic views of a pressure measuring apparatus during positive and negative pressure measurements, respectively, according to embodiments of the disclosed subject matter.
Figure 11B:
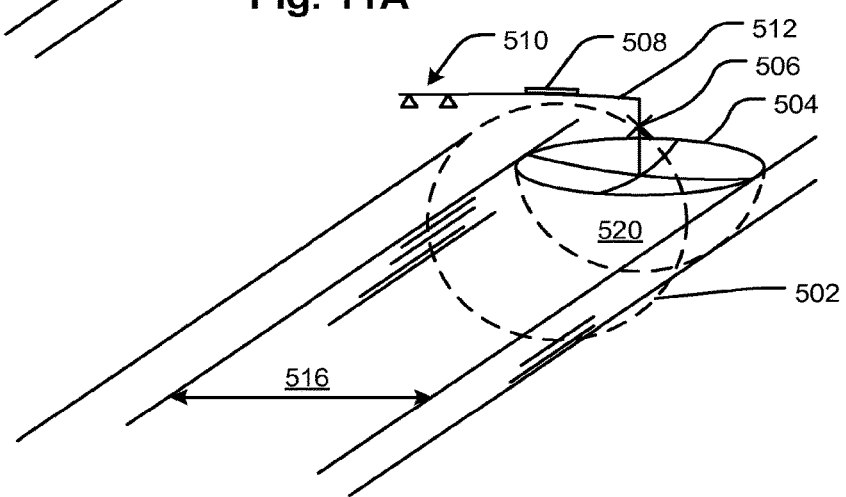
Figure 11C:
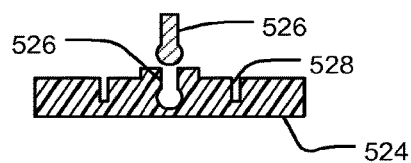
FIG. 11C shows an alternative mechanism for attaching a force measurement member to a diaphragm according to embodiments of the disclosed subject matter.

FIGS. 11A and 11B show schematic views of a pressure measuring apparatus 512 during positive and negative pressure measurements, respectively, according to embodiments of the disclosed subject matter.

Pressure measuring apparatus can have a measuring arm 510 supported by two points, for instance, and with a strain gauge 508 on an upper surface thereof. Pressure measuring apparatus 510 can be connected to diaphragm 504 via a disconnectable connection 506, which can be formed by engagement between a mechanical engagement member of the pressure measuring apparatus 510 and an engagement feature of the diaphragm 504, such as projection 464 shown in FIGS. 10E through 10F.

Engagement of the diaphragm 504 and the pressure measuring apparatus 510 can be provided by at least one of a projection integral with the diaphragm 504 or the pressure measuring apparatus 510, a magnet, a ferromagnetic material or member, a mechanical fastener for example, a Velcro fastener, a hook, an eye, a threaded recess, a threaded projection, a blade lock, a snap, and a surface or surfaces with an adhesive face. For example, FIG. 11C shows an alternative mechanism for attaching a force measurement member of the pressure measuring apparatus 510 to a diaphragm, whereby, opposite a second face 524 of the diaphragm is a recess 526 formed on a first face of the diaphragm for locking or removably locking with a mechanical engagement member in the form of a projection 526 with an enlarged end portion. The first face of the diaphragm can also include a flexibility promoting groove 528.

Additionally, FIGS. 11A and 11B show schematically the concept of the transition down in volume from a full cylindrical portion 502 corresponding to an inlet or input portion of the pod (e.g., port 472), for example, to a half cylinder portion 520 corresponding to the portion of the flow/fluid channel of the pressure pod associated with the inner or first surface of the diaphragm 504. The diameter of the diaphragm 504 may be about the same as a half cylindrical recess, as the inner wall of the fluid chamber may be no more than the distance 516 so as to provide positive or neutral draft to all the pins for removal thereof.

FIG. 12A is a schematic diagram of a pressure pod and force measurement assembly according to embodiments of the disclosed subject matter. Some components in FIG. 12A are labeled with the same numerals as used in prior figures so they will not be described again.

Component 540 can represent a machine chassis or support having at an end thereof a mating receiver 533 optionally an extension 515 (depending upon whether internal or external connection) as well as a guide pattern 536. The mating receiver 533 and optional extension 515 can have a connection member 534 for connecting to a connection member 532 of diaphragm 504. Pressure pod body 530 can have a receptacle 538 for mating and/or alignment with guide pattern 536. Component 542 can be a mechanism that puts connector 534 in a state that allows it to connect with connection member 532 of diaphragm 504.

For instance, component 542 can cause a member 550 to act on an engagement mechanism 552 such that the engagement mechanism 552 can be positioned for engaging the connection member 532 of diaphragm 504. FIG. 12B is a schematic diagram of a pressure pod 530 and force measurement assembly showing a mechanism 550 for placing a jaw-type attachment mechanism 552 in a receptive state according to embodiments of the disclosed subject matter. In order to place attachment mechanism 552 in position for engagement with connection member 532 of diaphragm 504, mechanism 550 acts on attachment mechanism 552 to place it in an open state, whereby its "jaws" are opened sufficiently to allow frictional engagement portions thereof to be moved to an engagement position around the connection member 532. Once in position, in operation, the jaws may be closed around the connection member 532 to engage and "grasp" the connection member 532.

FIGS. 12C and 12D are schematic diagrams of a force measurement assembly showing an alternative mechanism for placing a jaw-type attachment mechanism in an operational state and a receptive state, respectively, according to embodiments of the disclosed subject matter. Some components in FIGS. 12C and 12D are labeled with the same numerals as used in prior figures so they will not be described again.

A linear actuator 566 (e.g., a cam actuator) operates to move a movable portion 562 thereof to act on a lever 564 with a fulcrum 565 to move apart the "jaws" 560 about fulcrum 567 and thereby place the jaw-type attachment mechanism in a receptive state for placement with respect to the connection member 532 of the diaphragm. When the linear actuator 566 moves its movable portion 562 to the position shown in FIG. 12C, the jaws of the jaw-type attachment mechanism are caused to close around the connection member 532 of the diaphragm for pressure sensing operation. Optionally, movable portion 562 can be held in position to lock the jaws in a sufficiently tight engaged position with the connection member 532 of the diaphragm.

Figure 13A:
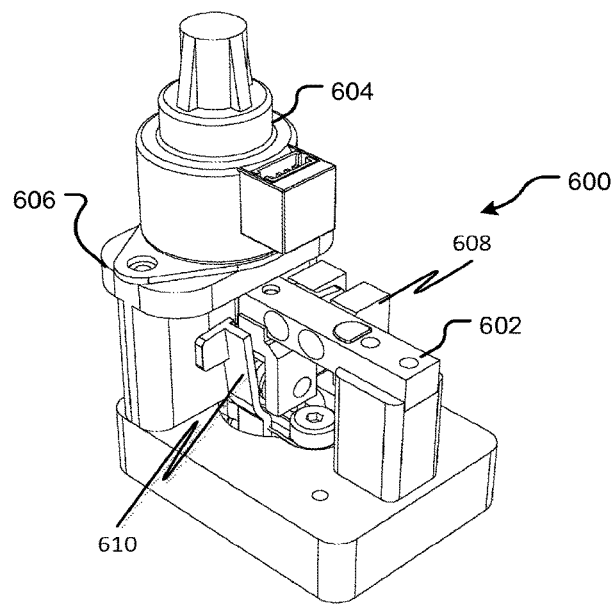
FIGS. 13A and 13B are perspective overhead and bottom views, respectively, of force measurement device according to embodiments of the disclosed subject matter.
Figure 13B:
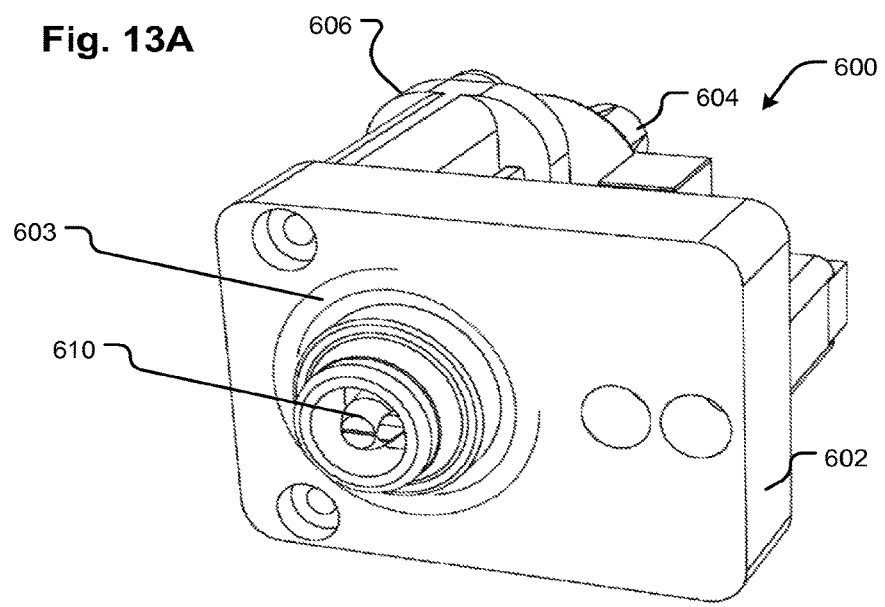
Figures 13C, 13D:
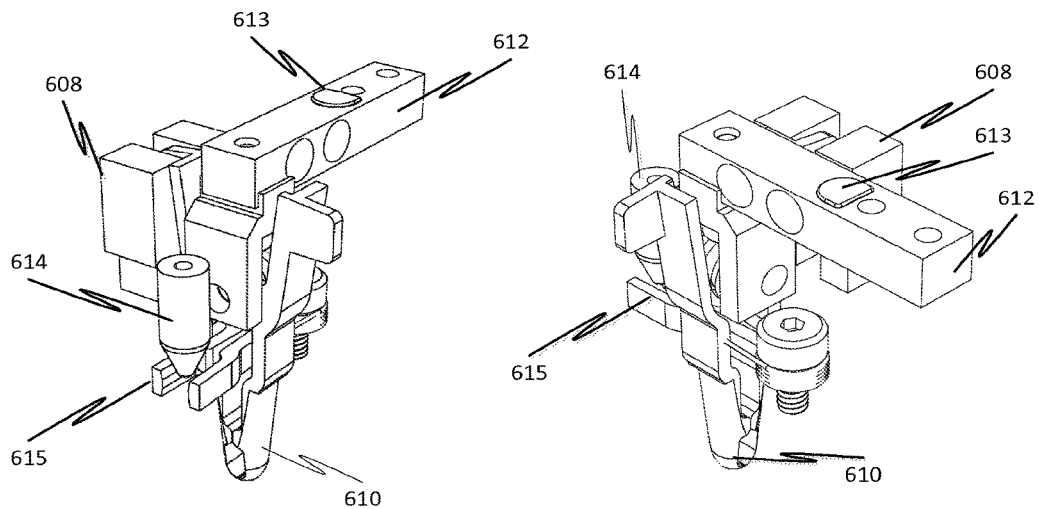
FIGS. 13C and 13D are views of portions of the force measurement device shown in FIGS. 13A and 13B, showing, among other things, a mechanical engagement member of the force measurement device.

FIGS. 13A and 13B are perspective overhead and bottom views, respectively, of force measurement device 600 according to embodiments of the disclosed subject matter. FIGS. 13C and 13D are views of portions of the force measurement device shown in FIGS. 13A and 13B, showing, among other things, a mechanical engagement member of the force measurement device.

Generally speaking, force measurement device 600 can include a base or chassis 602 with an O-ring 603, a linear actuator 604 supported by a bridge 606, a sensor portion 608, which can be an optical sensor, and a jaw-type attachment mechanism 610. Force measurement device 600 can also include a beam 612 with a strain gauge 613 coupled on a top surface thereof to detect a force associated with pressure-induced movement of a diaphragm operatively coupled to the beam 612 as set forth herein. Pusher 614 is attached to linear actuator 604 and can be caused to act on spreader 615 to open and close the jaws of the jaw-type attachment mechanism 610. The beam may be supported as a cantilever.

Figure 14A:
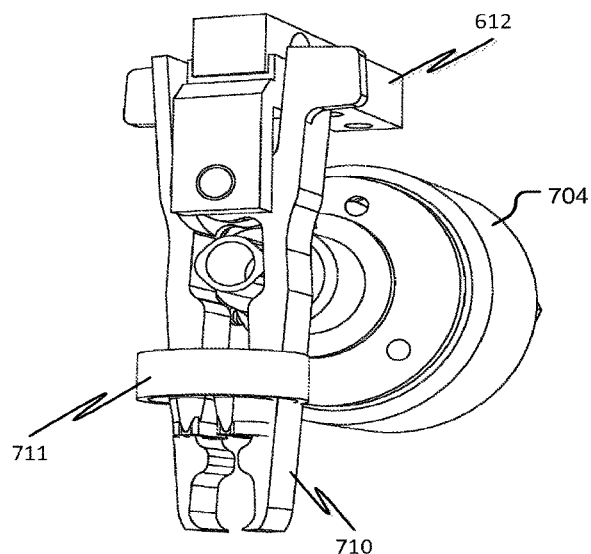
FIG. 14A is another embodiment of a mechanical engagement member portion of a force measurement device according to of the disclosed subject matter.

FIG. 14A is another embodiment of a mechanical engagement member portion of a force measurement device 700 according to of the disclosed subject matter. In particular, FIG. 14A shows another configuration of jaw-type attachment mechanism 710 that is operative with a rotary actuator 704. Optionally, an elastic band 711 may be employed to assist with closing and/or engagement of the jaws to a connection member of the diaphragm. Optionally or alternatively, a spring or springs may be used to assist with closing and/or engagement of the jaws to the connection member of the diaphragm.

Of course the jaw-type attachment mechanisms shown herein can be any suitable configuration. For instance, the jaw-type attachment mechanisms can be a single spring or resilient piece stamped out of a piece of steel (e.g., in the form of tongs or tweezers).

Figure 14B:
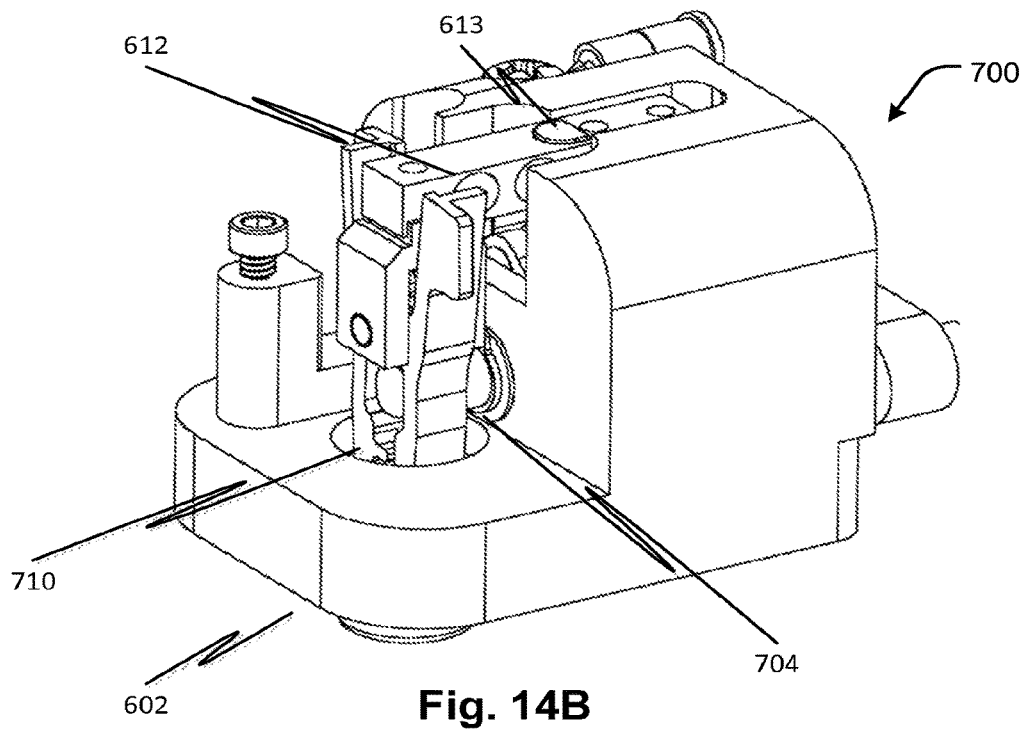
FIGS. 14B and 14C show view of a force measurement device configured with the mechanical engagement member portion shown in FIG. 14A.
Figure 14C:
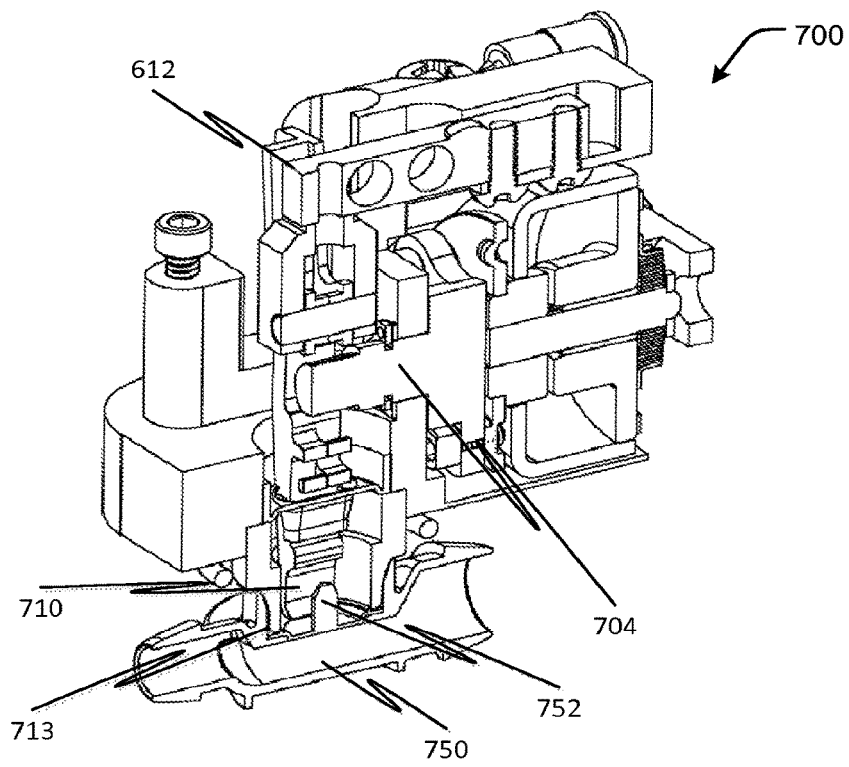

FIGS. 14B and 14C show view of a force measurement device 700 configured with the mechanical engagement member portion shown in FIG. 14A and also with the rotary actuator 704. FIG. 14C additionally shows, in cross section, force measurement device 700 positioned for operation with a pressure pod 750, such as those shown in FIGS. 10E, 10F, and 10G and described herein. Some components in FIGS. 14B, 14C, 14D, and 14E are labeled with the same numerals as used in prior figures so they will not be described again.

Figure 14D:
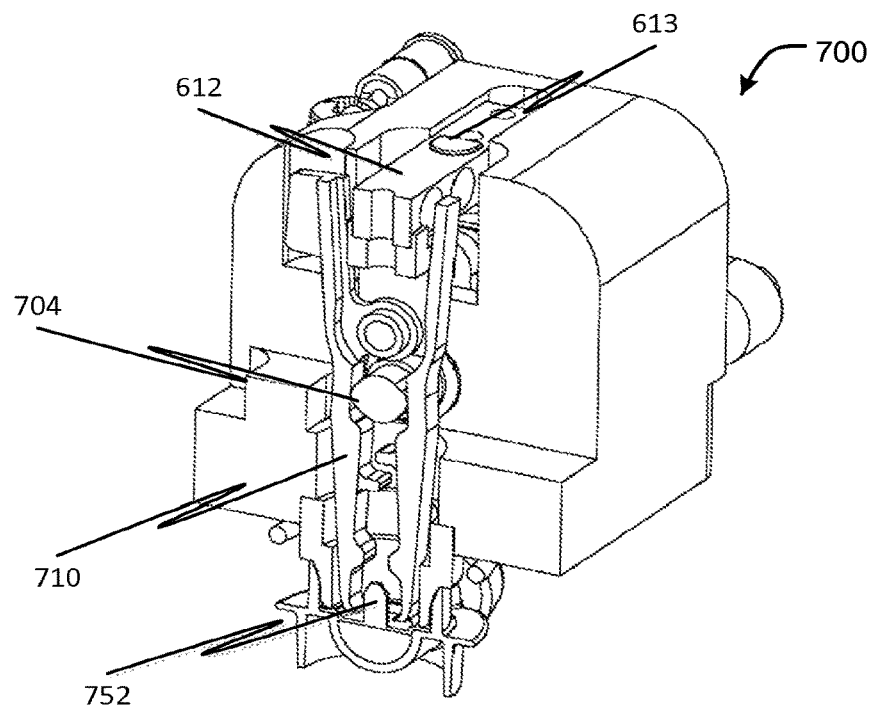
FIGS. 14D and 14E show different states of the mechanical engagement member portion shown in FIG. 14A, with FIG. 14D showing an open or disengaged state of the jaws, and with FIG. 14E showing a closed or engaged state of the jaws.
Figure 14E:
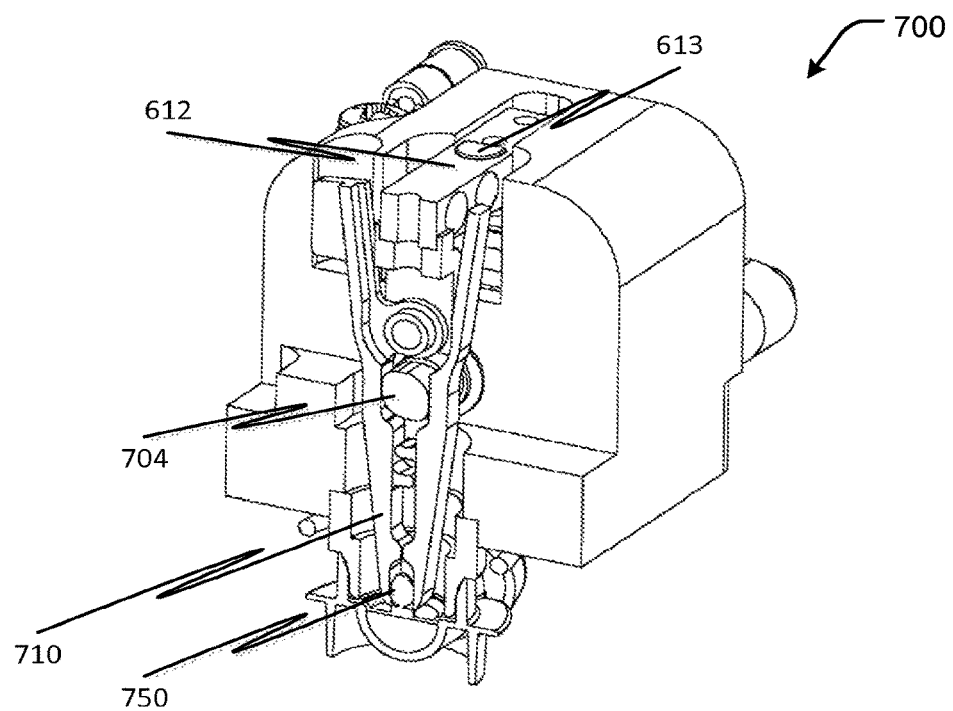

FIGS. 14D and 14E show different states of the mechanical engagement member 710 portion shown in FIG. 14A, with FIG. 14D showing an open or disengaged state of the jaws, and with FIG. 14E showing a closed or engaged state of the jaws, whereby the jaws are engaged and grip or pinch connection member 752 of the diaphragm.

Figure 15A:
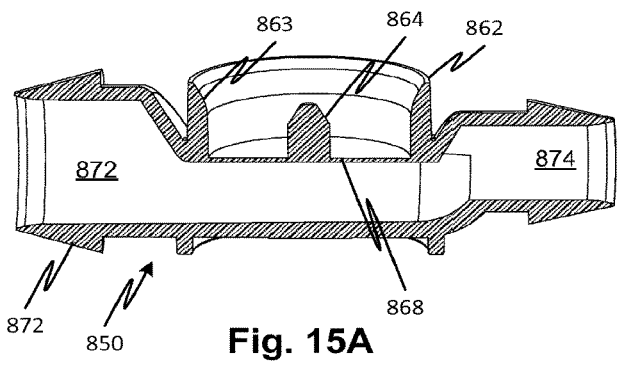
FIG. 15A shows a pressure pod according to embodiments of the disclosed subject matter showing features related to single-shot molding and having an integral diaphragm.

FIG. 15A shows a pressure pod 850 according to embodiments of the disclosed subject matter. Pressure pod 850 can be formed using a single-shot molding process in which the diaphragm 868 is formed integrally with the pressure pod body. A face of the diaphragm facing away from the fluid channel can have formed integrally with the diaphragm an engagement feature, such as engagement feature 864. Alternatively, that side of the diaphragm 868 can have another engagement feature as described herein. Tubing can be connected to fluid (e.g., blood) lines via 872, 874 as shown in FIG. 15A. The ports may also provide internal connections, the illustrated type being of the barb configuration in which tubes surround the outer rim of the port. The arrangement discussed above in which one tub may be larger diameter than the other to provide for a transition from one type of channel to another is provided in the present embodiment. For example, port 872 is larger which can accommodate a transition from a pump tubing segment to a smaller tube segment. In many types of tubing sets, a pump tube is used that has precise characteristics to ensure certain expected pumping performance which may include repeatability, durability, etc. Such segments may be larger diameter or smaller diameter than attached tubing segments. In such tubing sets, it may be desirable to locate a pressure sensor near the pump tubing segment or on both sides. For example by using pressure drop across the pump, it may be possible to mathematically calculate a predicted flow rate accurately. By using a pressure pod according to the disclosed embodiments in which the ports provide the additional function of transitioning different types of tubing, for example, different diameter tubing, beneficial cost savings may be achieved.

Figure 15B:
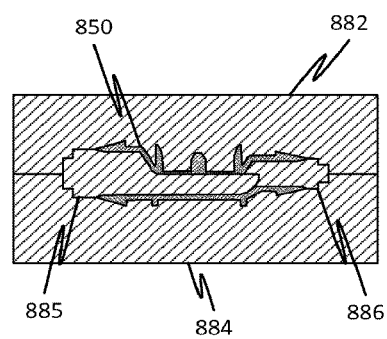
FIGS. 15B and 15C show mold embodiments which may be used to form the pod of FIG. 15A.
Figure 15C:
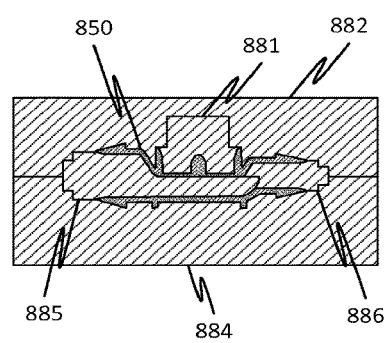

Referring to FIGS. 15B and 15C which represent alternative mold embodiments, the pod 850 of FIG. 15A may be manufactured in a single shot by inserting respective pins 885 and 886 into ports 872 and 874 of pod 850 as illustrated in FIGS. 15B and 15C and as discussed with regard to FIG. 10D and elsewhere herein. Then a single mold part 882 may be used to form the upper part and diaphragm 868 as shown in FIG. 15B or a pin 881 may be used to form the same portions, which include the annular rim 862. Another mold part 884 is used to form the lower part of the pod.

Another feature of the pod of FIG. 15A is the annular rim 862 which has a tapered inner surface 863 to guide a location boss on the measurement apparatus. For example, see element 713 which is an annular boss onto which the pressure pod 750 is placed. A similar feature is shown at 875 in FIG. 18A described further below. The boss may have a complementary tapered surface as shown in the above figures and as indicated in FIG. 18A at 876, for example. The annular rim 862 is preferably configured to provide a solid interference fit against a seat 898 (FIG. 18A) to ensure there is minimal movement in the Z-direction 821 such that repeatable measurements may be obtained. Alternative devices for limiting motion in the Z-direction are also possible, for example, one or more interlocking détentes may be provided which encircles the middle portions between the distal and proximal portions of the annular rim and boss. Another alternative is to provide an active mechanism that grips a portion of the pod once positioned to limit the movement in the Z-direction. These alternatives are not illustrated in the drawings.

Figure 16:
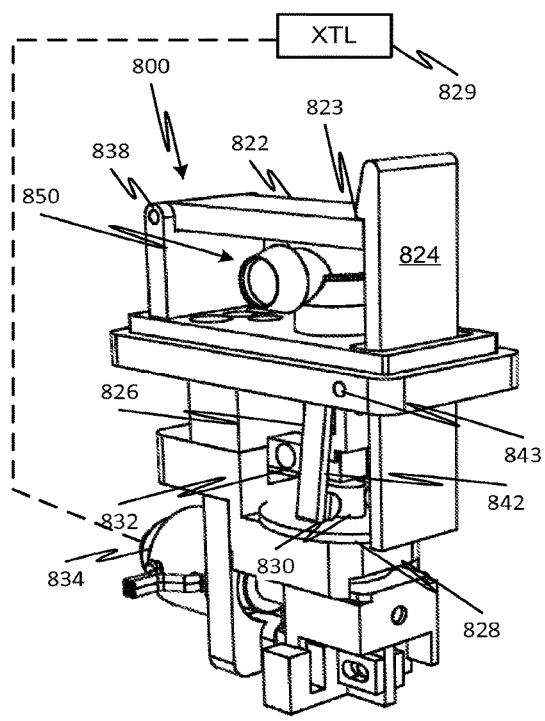
FIG. 16 shows a pressure measurement assembly for using the pod of FIG. 15A and other similar devices illustrated herein.

FIGS. 16, 17, and 18 show a pressure measurement assembly for using the pod of FIG. 15A and other similar devices illustrated herein. A retention bar 822 pivots on a hinge 838 to force pod 850 against a seat 898. The retention bar 822 is held down by a latch 824 which may have one interfering edge 823 to hold the latch down and urge it against the seat 898. Alternatively, retention bar 822 may be held in position by fitting into a notch 825 providing retention edges 823 and 891 above and below the bar 822 to prevent movement in the Z-direction as illustrated in FIG. 19. Another arrangement may generate a constant force against the pod 850 using a resilient member or spring. For example, as shown in FIG. 20, the retention bar 822 may include a leaf spring 827 configured to urge the pod 850 in the Z-direction with constant force. Instead of a spring the pod may have a spring-like feature. Alternatively, instead of a leaf spring, a piece of elastomeric material may be used.

Referring to FIGS. 16, 17 and 18, cams 830 and 828 may be driven by a motor 834 to open and close attachment mechanism 842, which has a gripper claw 837 that grips the engagement feature 464, 864 of the pod 850. Cams 830 and 826 may be provided on a single shaft which may be driven by a crank element 870 affixed thereto by the motor 834. The motor may be rotational or linear and in the present embodiment is a linear motor that forces the crank element 870, for instance, to rotate the cams 830 and 826. Cam 828 rotates to secure the latch 824 which pivots on a hinge 843. Thus, when a radially maximal portion of the cam abuts the lower end of the latch 824, the upper end is held in position to secure the retention bar 822. Beam 832 has a strain gauge attached thereto. Beam is connected to attachment mechanism 842 and is flexed by the change in pressure in the pod 850 as described in previous embodiments. The beam 832 may be supported as a cantilever as in earlier embodiments. The smaller cam 830 rotates to open the attachment mechanism 832 in a scissor fashion. The cams 828 and 830 are positioned such that the latch 824 is secured as the attachment mechanism 842 is closed around the engagement feature. Standoffs 867 may be provided in the present and other embodiments to prevent the gripper claw 837 from closing too much and cutting the engagement feature. Also, the gripper claw 837 may have a recess end as indicated at 839 of FIG. 18B to further reduce the risk of damaging the engagement feature 864.

A controller 829 may have an input device that allows a user to generate a command signal to open the device 800 to emplace a pod 850. The controller may in turn drive the motor 834 to release the latch and the retention bar which may then be lifted by the user. Simultaneously, according to the description of the cams 828, 830, the attachment mechanism 842 opens enabling the insertion of the attachment feature 864. The pod 850 may then be placed on the boss described above and the retention bar 824 rotated downwardly. Then a command to engage may be entered on the input device and the controller may cause the motor to rotate the cams to close the engagement mechanism 842 and engage the latch 824. Note that in the embodiment of FIGS. 16-18, instead of mechanical interlock between the engagement mechanism 826 (which is attached to the gripper) and the latch 924, the two mechanisms may be activated independently by the controller with sensors used to determine if the latch has been closed before the gripper is engaged.

FIG. 21 illustrates an embodiment of a pressure pod assembly 900 in which a strain gauge is attached directly to the diaphragm and an electrical connector 910 connects leads to and from a driver circuit (not shown) for reading pressure signals to form an embodiment that may be included as part of a disposable circuit. An electrical connector 910 has conductors 912 that connect electrically with conductive leads 908 of strain gauge 906 attached to a thin flexible metal plate 914 that is directly bonded to the diaphragm 916 of pod 920. The leads 904 may be attached to tubing of a tubing set of an embodiment in which the connector 910 and pod are attached to form a disposable set. Alternatively, the electrical connector may be a separate component 911 that is attached to the remainder of the assembly, including the pod 920, which forms the disposable set.

Figure 22:
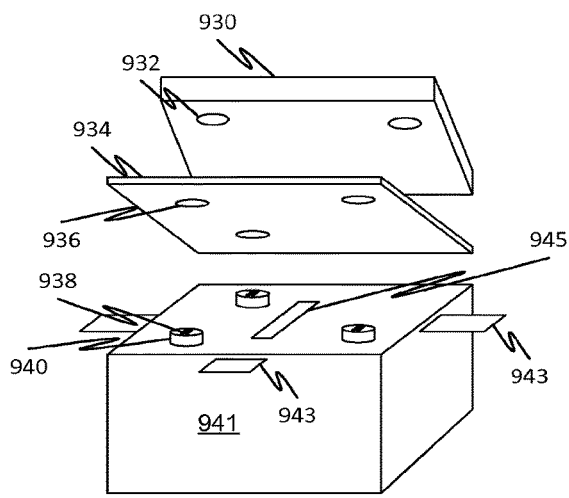
FIG. 22 shows a machine with a cartridge having multiple pods and a retention fixture attachable thereto.

FIG. 22 shows a machine with a cartridge having multiple pods and a retention fixture attachable thereto. A machine 941, for example a blood treatment machine, peritoneal dialysis cycler, filtration system or other fluid conveying device has an array of pressure sensing stations 940 each with an attachment device as in any of the disclosed embodiments, for example, the gripper claw 837. The associated mechanism for measuring pressure may be housed with other components of the machine 941 in a housing with the alignment boss 938 protruding above a surface of the housing. A fluid circuit cartridge 934 has fluid channels such as tubes attached or embedded therein. The fluid circuit has pressure pods 936 which are held onto the bosses 940 by a latching door 930 with respective fixtures 932 for engaging the pods 936. Latch mechanisms 943 may be provided to hold the latching door 930. One or more other actuators or sensors 945 may also be engaged by the latching door. Instead of a latching door or panel other types of hold-down devices may be used and these may vary in number. Instead of a cartridge, other types of fluid circuit structures may be provided including ones with no support other than the tubes and circuit components themselves.

Figure 23A:
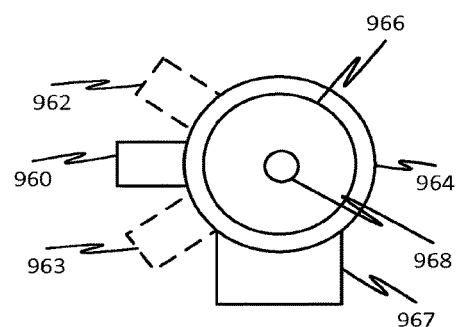
FIGS. 23A and 23B show alternative arrangements of ports illustrating variations on the disclosed embodiments.
Figure 23B:
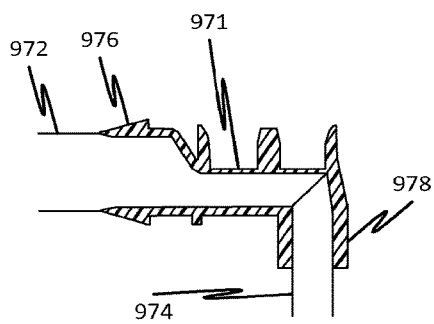

FIGS. 23A and 23B show alternative arrangements of ports illustrating variations on the disclosed embodiments. It should be apparent from the disclosure that the ports of the pod embodiments do not need to be diametrically opposed and that other arrangements of mating pins can provide for ports at different angular orientations, for example, as indicated at 960, 962, and 963. A major port 967 whose major dimension coincides with that of the diaphragm 966 is provided as in other embodiments. An engagement feature may also be as discussed in other embodiments including the alternatives such as a magnet, Velcro., or other attachment.

FIG. 23B shows an embodiment with a port 978 that is aligned with an axis that forms an angle with respect to the plane of the diaphragm 971. The diaphragm is molded with the aid of a pin whose outline is shown by the lines 972. The port 978 internal opening is formed with a pin whose outline is shown at 974. The resulting ports 976 and 978 may thus form a right angle, for example, with one port being at a right angle to the diaphragm plane.

In the disclosed embodiments, it may be observed that a low volume pressure pod may be configured by employing a direct connection of the diaphragm to a force transducer. Without a compressible fluid between the diaphragm and the force transducer, the compliance that has to be overcome to generate a pressure signal is near zero and so the size and excursion of the diaphragm can be minimal. Embodiments in which the chamber is formed by a pin whose maximum dimension is that same as the diaphragm diameter are described herein. The small size is enabled by the direct connection and as a further result the molding process has been simplified, with one embodiment being formed in a single molding step with two mold parts. Of course variations of the disclosed molding operations and products are possible and also enabled by the disclosure. By having a small diaphragm, the flow channel and in-line chamber beneath the diaphragm can be formed such that there is very low or no change in channel diameter or flow area which minimizes turbulence. This is particularly desirable in the context of blood flow because it lowers the risk of thrombogenesis.

It is therefore, apparent that there is provided, in accordance with the present disclosure, a device, method, and system which provides for pressure measurement and for making and using the same. Many alternatives, modifications, and variations are enabled by the present disclosure. Features of the disclosed embodiments can be combined, rearranged, omitted, etc. within the scope of the disclosed subject matter to produce additional embodiments.

For example, although the pressure pods described generally employ an alignment and seating mechanism including an annular boss on the measurement mechanism and annular rim of the pod, the pair may employ other arrangements to achieve the functions described. For example, the pod may be configured with a boss that fits into a recess in the measurement mechanism. The measurement mechanism term applies to all the devices described herein that engage with a pod and which include a force measurement transducer, for example, the structure at 800 in FIG. 16 apart from the pod.

Figures 24A, 24B:
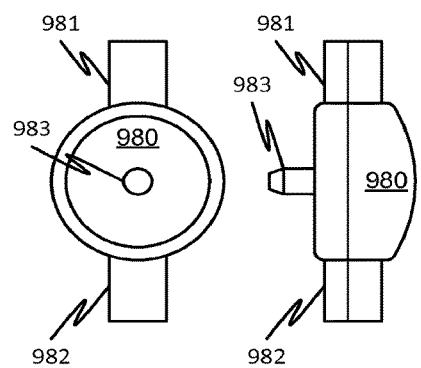
FIGS. 24A and 24B show an improvement of a pressure pod according to an embodiment of the disclosed subject matter.

Also note that although the embodiments described are principally provided with the ability to measure negative pressures as well as positive, other embodiments employing features of the disclosed subject matter may also be based on the present disclosure. For example, instead of attaching the force sensor to the diaphragm to allow for positive and negative pressure measurement, the force sensor may merely be held against the diaphragm to allow positive pressures to apply a force. Thus simpler embodiments may be produced. Also note that although the disclosed pressure pods emphasize the embodiments that are based on simple molding techniques, more traditional configurations with an internal chamber that is larger than either of the ports and which therefore need to be assembled or require more complicated molding operations can still have features of the disclosed embodiments. For example, FIGS. 24A and 24B, show a pod 980 that may be formed by welding together molded parts and therefore is capable of having a larger diaphragm and chamber than the ports 981, 982. The pod 980 may have an engagement element 983 as in above-described embodiments or may have a directly connected transducer as in the embodiment of FIG. 21. Alternatively such embodiment may have a magnetically coupled connection between a force transducer and the diaphragm.

Figure 25:
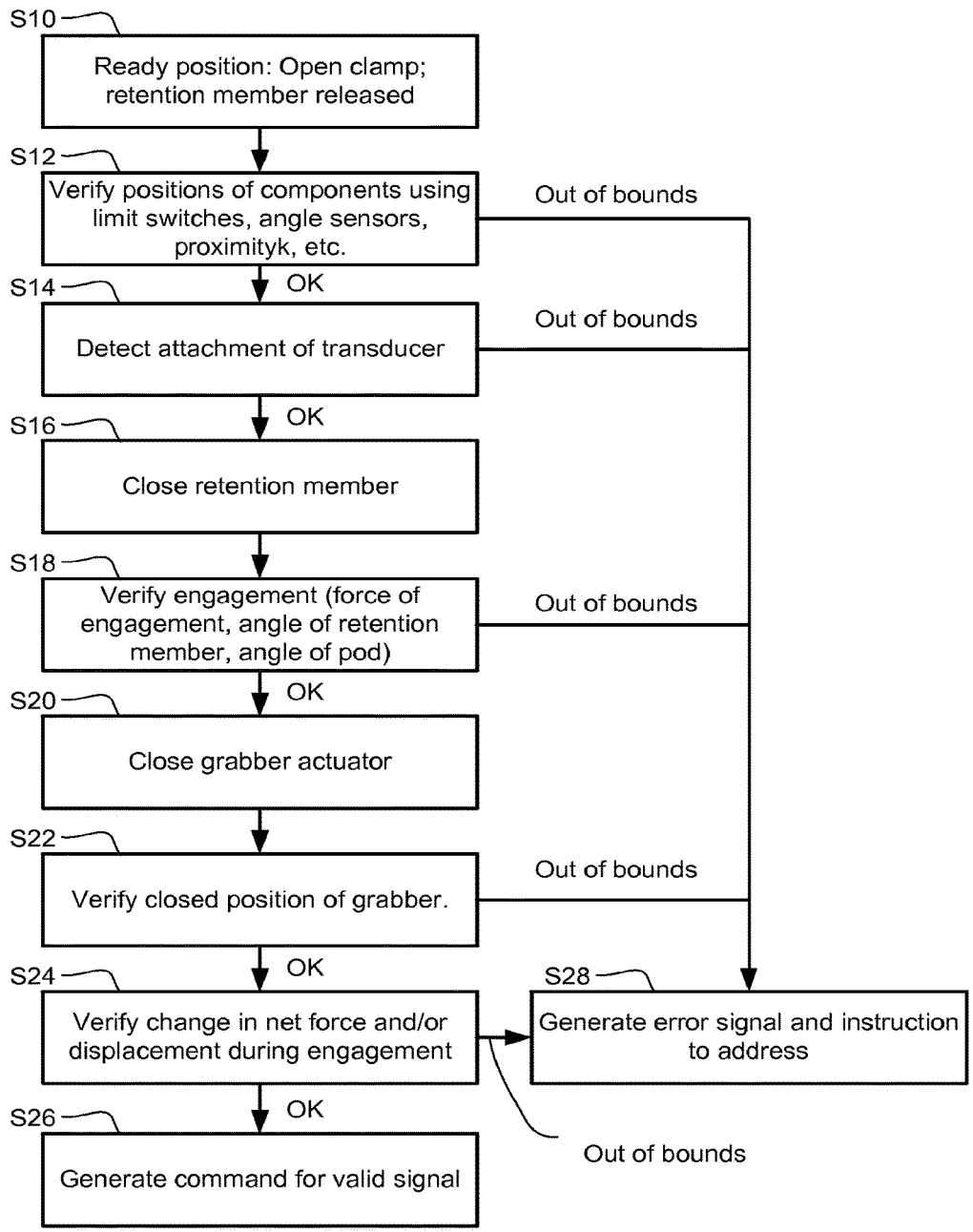
FIG. 25 shows a flow chart of various embodiments of a control of a pressure measuring system.

Referring to FIG. 25, a control procedure for embodiments of the pressure measurement system described herein begins with the transducer mechanism in a ready position with an engagement element in a ready position. For example the clamping mechanism jaws may be in the open position and any retention features in a released position such that the flow channel device (e.g., pod) can be attached to the transducer mechanism. The mechanical positions of the various elements may be verified at S12 and if verified, an output signal indicating read status may be generated. This ready signal may be converted to a display output indicating the readiness of the apparatus to receive a fluid circuit or just the pressure pod. Then control proceeds to S14. The positions of the jaws of the gripper mechanism, for example, may be verified using angle sensors or optically using an optical encoder or imager. If the transducer mechanism is not verified as ready, an error signal is generated at S28. The error signal may include the output of instructions to compensate or fix the problem.

At S14, the attachment of the fluid channel or fluid circuit or pod may be detected. S14 is optional or could be done after the closure of a retention member at S16. After a retention mechanism, such as the retention member discussed above, is engaged at S16, the proper mounting of the fluid channel is verified at S18. This may include the detection of the force with which the fluid channel component (e.g. pod) is pressed against the chassis and comparison to a predefined range by the controller. In addition, or alternatively, the angle or position of the retention element may be verified optically for example using laser scanner imaging or optical imaging. At S20, if detected configuration meets a predefined specification, the engagement mechanism (e.g., gripper mechanism) is actuated and at S22 the completion of the engagement verified by sensors. The same devices as used for in previous steps may be employed for the S22. In addition, any change in the configuration of the flow channel device as a result of the engagement of the actuator (e.g. gripper) may be detected and alarmed as necessary. For example, any net displacement of the engagement member may be detected optically or a force exerted on the gripper mechanism may be detected that is out of a predefined magnitude range or direction may be sensed at S26 and corresponding action taken. Once S26 step is completed and conditions verified to be within bounds, the controller may generate a ready command signal indicating the detected parameters at all points of the sequence were within predefined range.

Several terms are used interchangeable, and some are hypernyms of others used in the present specification. For example, engagement mechanism or member is generic to gripper which is generic to claw, but it should be clear that these are abstractions of the detailed embodiments that include 560, 610, and the like, though the more generic terms are intended to encompass more embodiments than the more specific terms. Similarly, the term flow channel is generic to pod. The features of the disclosed subject matter may be applied to flow channels that are incorporated in a fluid circuits with many elements and may be integrated in number in such configurations. The pod configuration is not essential to the provision of all the features described, so for example, a cartridge structure may have a flow channel therein and a low compliance diaphragm forming a wall of the channel which may take advantage of the teachings of presently disclosed subject matter.

Among the features described above which may be noted are the following.

Figure 24C:
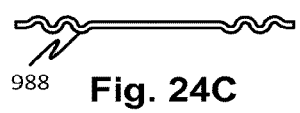
FIG. 24C shows an optional diaphragm that may be used with the embodiment of FIGS. 24A and 24B.

1. A mechanism is provided for immobilizing the diaphragm support. This feature is useful where, as here, the diaphragm is flat and therefore will experience a restoring force with only a very minimal displacement. Alternative embodiments such as shown in FIGS. 24A and 24B can have a corrugated diaphragm as shown in FIG. 24C in which case, the support of the diaphragm support can be more compliant. The immobilization is provided in embodiments, for example, by the rigid pod housing supporting the diaphragm perimeter, the annular rim (e.g., 862) and the seat on the chassis of the transducer mechanism (e.g., 898).
2. The retention element or protrusion may be configured to present no position bias that would create a force upon engagement by the gripper mechanism. For example, the sides of the protrusion embodiments shown are smooth featureless allowing the edges of the gripper to engage it where the edges of the gripper initially make contact with the engagement member. Contrast this with a member having a recess, which could bias the diaphragm upon being engaged by a mating gripper mechanism.

3. The gripper has a pivot access that is remote from the engagement member so that the rotation after initial engagement produces minimal axial movement of the diaphragm as a result of the pivoting of the jaws after the initial contact with the engagement member.
4. The rigid housing of a pod provides additional support to the diaphragm thereby further ensuring the diaphragm support is immobile with respect to the transducer mechanism chassis. Note it is assume the chassis is the base that supports the strain gauge element so that the movement of the diaphragm relative to the chassis translates to pressure indications.
5. A centering mechanism, such as the combination of an annular rim on the pod housing and the boss on the transducer chassis with associated tapered surfaces, ensures the engagement member is positioned in the transducer mechanism.
6. The immobilization features and direct connection between the diaphragm and transducer make it possible to use a low compliance diaphragm. This further enables the molding techniques described above. It also enables a small size diaphragm which provide benefits of allowing a small diameter flow channel and thereby the reduction of flow decelerations that attend the use of a conventional pod. The ability to use a diaphragm of low compliance is also associated with the use of a low aspect ratio channel. In the disclosed embodiments, the aspect ratio is below 3 and in some embodiments, below 4.
7. The low aspect ratio in combination with small flow area provides a high velocity, low strain rate fluid dynamics which are highly friendly to blood flow. This is combined with a flow area transitions of low magnitude which correspond to low acceleration/deceleration and concomitant low turbulence. For example, the pod embodiments may have a diaphragm diameter between 5 and 10 mm, a first port diameter between 5 and 10 mm and a second port diameter between 3 and 8 mm. in an exemplary embodiment, the first port is 8 mm, the diaphragm is 8 mm, the second port is 5 mm which corresponds to hydraulic diameter of the first port being about 8 mm, the internal channel below the diaphragm about 5 mm and the second port, 5 mm. The maximum aspect ratio of the latter embodiment is 2. The path through the embodiments is minimally-tortuous as well. Thus the variation in hydraulic diameter, it will be seen, can be only 60% while still providing for positive or neutral draft shape that allows the single-shot molding to be used for fabrication. Note the calculations assume the shape of the pod embodiment illustrated at 850 in the drawings with cross section as discussed with reference to FIGS. 12A and 12B.
8. The flat internal surface of the diaphragm provides a neutral draft for removal of a molding pin, but it also has benefits in terms of blood flow in that it presents a smooth surface to the flow which also minimizes turbulence.

In embodiments, the aspect ratio of the flow channel of the pressure pod is less than three. In embodiments, the maximum dimension of the channel from port to port is 20 mm. In further embodiments, the maximum dimension is 15 mm. In still further embodiments, the maximum dimension is 10 mm. In embodiments the maximum dimension is 8 mm. In embodiments, the maximum aspect ratio from port to port is 2. In a particular embodiment the maximum dimension of 10 mm from port to port is combined with the maximum aspect ratio of 2. In any of the embodiments, the hydraulic diameter varies by no more than 100% and in further embodiments, the hydraulic diameter varies by no more than 80% and in still further embodiments by no more than 60%. The hydraulic diameter from port to port, in embodiments, may range from 5 to 15 mm. In embodiments, the hydraulic diameter remains at all points along the flow path, in a range between 4 mm and 10 mm. In embodiments, the hydraulic diameter remains at all points along the flow path, in a range between 5 mm and 8 mm.

All of the pod configurations may be modified to have any of a variety of shapes and the pod shape is not necessarily essential to providing at least some of the features described herein. Generally, a variety of self-supporting flow channels can be configured in any of a variety of shapes, with a diaphragm in a wall of the channel, and configured to provide the low internal volume, negative pressure-measuring capabilities of the embodiments described herein. Such flow channels could be formed as part of a larger network structure that has other flow elements such as valves, sensors, and/or pumping sections, for example.

Various mechanisms for immobilizing the housing of the pressure pod can be used. In addition to the détente and retention bar approaches, the pod may be secure by a retention clamp which engages a flange at the mouth of the annular rim, vacuum suction, by a magnetic force, or by any of a variety of mechanisms.

It will be appreciated that the modules, processes, systems, and sections described above can be implemented in hardware, hardware programmed by software, software instruction stored on a non-transitory computer readable medium or a combination of the above. For example, a method for generating a pressure signal can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their subcomponents or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with knowledge of medical devices and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, pressure measurement devices methods and systems including control system which may include programmable processors and related effecters. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

Furthermore, certain features of the disclosed embodiments may sometimes be used to advantage without a corresponding use of other features. Accordingly, Applicants intend to embrace all such alternatives, modifications, equivalents, and variations that are within the spirit and scope of the present disclosure.

What is claimed is:

1. A method of manufacturing a molded pressure measuring pod that is configured to measure positive and negative pressure of a fluid that flows through the molded pressure measuring pod, the method comprising:
   providing first and second major mold parts having recesses defining major parts of a housing of the pressure measuring pod;
   inserting a first pin and a second pin, both having a positive draft, into the first and second major mold parts, the first pin and the second pin being shaped to define a first port and a second port and a flow channel that is configured to permit flow between the first port and the second port through the molded pressure measuring pod;
   the first pin having a flat major face that defines an internal surface of a diaphragm, the diaphragm being configured to flex in response to pressure in the molded pressure measuring pod and to prevent flow of fluid through the diaphragm;
   closing the first and second major mold parts with the first pin and the second pin therebetween;
   injection molding the housing of the pressure measuring pod; and
   separating the first and second major mold parts;
   withdrawing the first pin and the second pin; and
   removing the housing of the pressure measuring pod from the first and second major mold parts.

2. The method of claim 1, wherein the withdrawing the first pin and the second pin opens ports in the housing that communicate through the housing.

3. The method of claim 1, wherein one of the first pin and the second pin has a major dimension that is larger than, or equal in size to, the diaphragm.

4. The method of claim 2, wherein one of the first pin and the second pin has a major dimension that is larger than, or equal in size to, the diaphragm.

5. The method of claim 1, wherein one of the first pin and the second pin has a major dimension that is larger than, or equal in size to, a diameter of the diaphragm.

6. The method of claim 2, wherein one of the first pin and the second pin has a major dimension that is larger than, or equal in size to, a diameter of the diaphragm.

7. The method of claim 1, wherein the diaphragm has an engagement feature on an outside surface thereof.

8. The method of claim 2, wherein the diaphragm has an engagement feature on an outside surface thereof.

9. The method of claim 3, wherein the diaphragm has an engagement feature on an outside surface thereof.

10. The method of claim 4, wherein the diaphragm has an engagement feature on an outside surface thereof.

11. The method of claim 5, wherein the diaphragm has an engagement feature on an outside surface thereof.

12. The method of claim 6, wherein the diaphragm has an engagement feature on an outside surface thereof.

13. The method of claim 7, wherein the engagement feature is a projection.

14. The method of claim 12, wherein the engagement feature is a projection.

15. The method of claim 1, wherein
   the inserting the first pin and the second pin includes positioning the first pin in direct contact with the second pin, such that a combined shape of the first pin and the second pin creates the flow channel through the molded pressure measuring pod.

16. The method of claim 14, wherein the inserting the first pin and the second pin includes positioning the first pin in direct contact with the second pin, such that a combined shape of the first pin and the second pin creates the flow channel through the molded pressure measuring pod.

17. The method of claim 1, further comprising:
inserting a third pin that defines an outer surface of the diaphragm before the injection molding; and
withdrawing the third pin.

18. The method of claim 16, further comprising:
inserting a third pin that defines an outer surface of the diaphragm before the injection molding; and
withdrawing the third pin.

19. The method of claim 1, wherein the injection molding includes
injecting a thermoplastic material that hardens into a rigid structure.

20. The method of claim 18, wherein the injection molding includes
injecting a thermoplastic material that hardens into a rigid structure.

* * * * *